US012679885B2

(12) United States Patent
Mammano et al.

(10) Patent No.: US 12,679,885 B2
(45) Date of Patent: Jul. 14, 2026

(54) COMPOSITION AND METHODS TO TREAT ECTODERMAL DYSPLASIA 2, CLOUSTON TYPE

(71) Applicant: SHANGHAITECH UNIVERSITY, Shanghai (CN)

(72) Inventors: Fabio Mammano, Padua (IT); Guang Yang, Shanghai (CN); Francesco Zonta, Shanghai (CN)

(73) Assignee: SHANGHAITECH UNIVERSITY, Shanghai (CN)

( * ) Notice: Subject to any disclaimer, the term of this patent is extended or adjusted under 35 U.S.C. 154(b) by 200 days.

(21) Appl. No.: 17/614,288

(22) PCT Filed: May 28, 2019

(86) PCT No.: PCT/CN2019/088689
§ 371 (c)(1),
(2) Date: Jun. 26, 2025

(87) PCT Pub. No.: WO2020/237491
PCT Pub. Date: Dec. 3, 2020

(65) Prior Publication Data
US 2022/0251179 A1      Aug. 11, 2022

(51) Int. Cl.
*C07K 16/18* (2006.01)
*A61K 39/00* (2006.01)
*A61P 17/00* (2006.01)

(52) U.S. Cl.
CPC .............. *C07K 16/18* (2013.01); *A61P 17/00* (2018.01); *A61K 2039/505* (2013.01); *C07K 2317/34* (2013.01); *C07K 2317/565* (2013.01); *C07K 2317/622* (2013.01); *C07K 2317/76* (2013.01)

(58) Field of Classification Search
None
See application file for complete search history.

(56) References Cited

FOREIGN PATENT DOCUMENTS

| | | |
|---|---|---|
| CN | 105566495 A | 5/2016 |
| EP | 1 308 458 A1 | 5/2003 |
| NL | 1019226 C2 | 4/2003 |

OTHER PUBLICATIONS

Messmer et al. Ocular Manifestations of Keratitis-Ichthyosis-Deafness (KID) Syndrome. Ophthalmology 2005;112:e1-e6. (Year: 2005).*

Protein Data Bank (PDB) under the accession codes 5WYM. pdb_00005wym, Crystal structure of an anti-connexin26 scFv (Year: 2017).*
Lee, Ming Yang, Allele-specific siRNA Therapy for KeratitisIchthyosis-Deafness Syndrome. Thesis for the degree of Doctor of Philosophy, University College London, 2018., pp. 1-191. (Year: 2018).*
Van Steensel et al. A Phenotype Resembling the Clouston Syndrome with Deafness Is Associated with a Novel Missense GJB2 Mutation. J Invest Dermatol 291-293, 2004. (Year: 2004).*
Garcia et al. From Hyperactive Connexin26 Hemichannels to Impairments in Epidermal Calcium Gradient and Permeability Barrier in the Keratitis-Ichthyosis-Deafness. Journal of Investigative Dermatology vol. 136, Issue 3, Mar. 2016, pp. 574-583 (Year: 2016).*
Extended European Search Report dated Mar. 22, 2023, EP 19930950. 1, 17 pages.
Kleopa, Kleopas "The Role ofo Gap Junctions in Charcot-Marie-Tooth Disease", The Journal of Neuroscience, vol. 31, No. 49, Dec. 7, 2011, pp. 17753-17760.
RCSB Protein Data Bank: "RCSB PDB—5WYM: 1, 2, 7-15 Crystal Structure of an Anti-Connexin26 svFv", Jan. 24, 2018, 3 pages.
Xu, Liang et al., Design and Characterization of a Human Monoclonal Antibody that Modulates Mutant Connexin 26 Hemichannels Implicated in Deafness and Skin Disorders, Frontiers in Molecular Neuroscience, vol. 10, Sep. 22, 2017, 19 pages.
Liu et al., "Novel mutations in GJB6 and GJB2 in Clouston syndrome", Clinical and Experimental Dermatology, Mar. 26, 2015, pp. 1-4, vol. 40, No. 7, 2015 British Association of Dermatologists.
Mhaske et al., "The human Cx26-D50A and Cx26-A88V mutations causing keratitis-ichthyosis-deafness syndrome display increased hemichannel activity", American Journal of Physiology-Cell Physiology, 2013, pp. C1150-C1158, vol. 304, The American Physiological Society.
Ressot et al., "Connexin32 Mutations Associated with X-Linked Charcot-Marie-Tooth Disease Show Two Distinct Behaviors: Loss of Function and Altered Gating Properties", The Journal of Neuroscience, Jun. 1, 1998, pp. 4063-4075, vol. 18, No. 11, 1998 Society for Neuroscience.
International Search Report and Written Opinion of the International Searching Authority issued in International Application No. PCT/CN2019/088689, mailed Feb. 26, 2020.

* cited by examiner

*Primary Examiner* — Maher M Haddad
(74) *Attorney, Agent, or Firm* — Foley & Lardner LLP

(57) ABSTRACT

The present technology relates generally to compositions and methods of preventing or treating diseases associated with mutant Cx26, Cx32, and/or Cx30 hemichannels. The present technology also relates to administering the anti-Cx26 hemichannel antibodies in effective amounts to treat a subject suffering from, or predisposed to, ectodermal dysplasia 2, Clouston type (OMIM No. 129500), Keratitis-ichthyosis-deafness syndrome (KIDS; OMIM No. 148210), and/or type X Charcot-Marie-Tooth neuropathy (CMTXI; OMIM No. 302800).

11 Claims, 16 Drawing Sheets

Specification includes a Sequence Listing.

EC2 loop

EC1 loop

EC1 loop

EC2 loop

Blood clearance curves

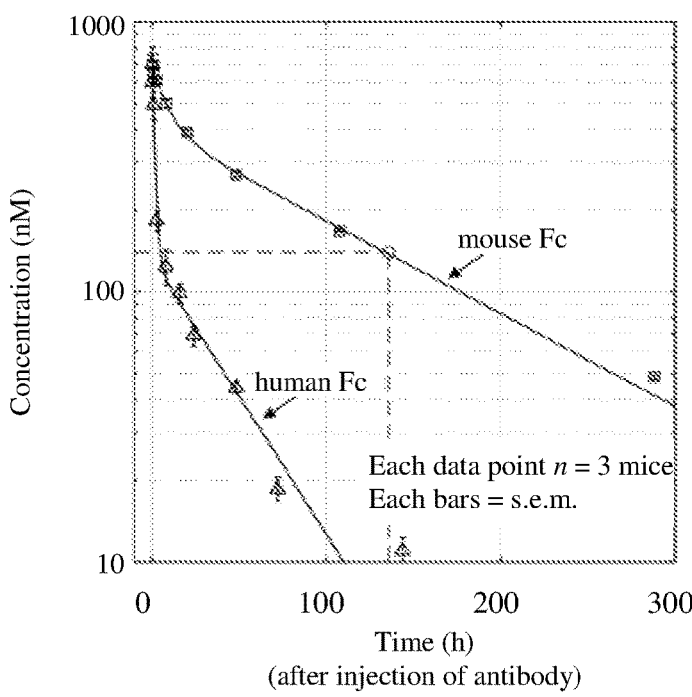

Antibody with Human-Fc
data fitted with:

$f(t) = A_1 \exp(-t / \tau_1) + A_2 \exp(-t / \tau_2)$

Coefficients (with 95% confidence bounds):

$A_1 = 675$ nM (607, 743)

$\tau_1 = 1.4$ h (1.1, 2.0)

$A_2 = 132$ nM (77, 187)

$\tau_2 = 43$ h (24, 213)

Antibody with mouse-Fc
data fitted with:

$f(t) = A_1 \exp(-t / \tau_1) + A_2 \exp(-t / \tau_2)$

Coefficients (with 95% confidence bounds):

$A_1 = 291$ nM (230, 352)

$\tau_1 = 9.5$ h (6.8, 16.1)

$A_2 = 402$ nM (338, 466)

$\tau_2 = 127$ h (101, 171)

mouse Fc human Fc

Each data point $n = 3$ mice
Each bars = s.e.m.

Time (h)
(after injection of antibody)

FIG. 7

Skin clearance curve

Time (h)

(after cream application)

COMPOSITION AND METHODS TO TREAT ECTODERMAL DYSPLASIA 2, CLOUSTON TYPE

CROSS REFERENCE TO RELATED APPLICATIONS

This is a U.S. National Stage Application under 35 U.S.C. § 371 of No. PCT/CN2019/088689, filed on May 28, 2019, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Dec. 21, 2021, is named 113536-0114_SL.txt and is 8,460 bytes in size.

TECHNICAL FIELD

The present technology relates generally to compositions and methods of preventing or treating diseases associated with mutant Cx26, Cx32, and/or Cx30 hemichannels. More particularly, the present technology relates to administering an effective amount of the anti-Cx26 hemichannel antibodies to treat a subject suffering from, or predisposed to, ectodermal dysplasia 2, Clouston type (OMIM No. 129500), Keratitis-ichthyosis-deafness syndrome (KIDS; OMIM No. 148210), and/or type X Charcot-Marie-Tooth neuropathy (CMTX1; OMIM No. 302800).

BACKGROUND

The following description is provided to assist the understanding of the reader. None of the information provided or references cited is admitted to be prior art.

Gap junctions are specialized intercellular connections between animal cells, which allow bidirectional transport of ions and signaling molecules between neighboring cells. Gap junctions are composed of closely packed pairs of transmembrane channels called the connexons or hemichannels, which include structurally related transmembrane proteins called connexins. Connexins, which are typically named based on their molecular weights, (e.g. Cx26 is the connexin protein of 26 kDa), contain four transmembrane domains, two extracellular loops (called EC1 and EC2) and cytoplasmic regions. Connexins form homo- or heterohexameric arrays to form the hemichannels. The hemichannels in the plasma membrane of one cell docks end-to-end with hemichannels in the membrane of a neighboring cell to form complete gap junctions. Gap junctions are essential for many physiological processes, such as the coordinated depolarization of cardiac muscle, proper embryonic development, and the conducted response in microvasculature.

SUMMARY OF THE PRESENT DISCLOSURE

In one aspect, the present technology relates to the treatment, amelioration or prevention of ectodermal dysplasia 2, Clouston type (OMIM No. 129500) in a subject in need thereof, through administration of therapeutically effective amounts of an antibody or antigen binding fragment thereof comprising a heavy chain immunoglobulin variable domain (VH) and a light chain immunoglobulin variable domain ($V_L$), wherein the $V_H$ comprises complementarity determining regions $V_H$CDR1, $V_H$CDR2 and $V_H$CDR3, wherein the $V_H$ CDR1 comprises an amino acid sequence set forth in SEQ ID NO: 3, $V_H$ CDR2 comprises an amino acid sequence set forth in SEQ ID NO: 4, and $V_H$ CDR3 comprises an amino acid sequence set forth in SEQ ID NO: 5; and wherein the $V_L$ comprises complementarity determining regions $V_L$CDR1, $V_L$CDR2 and $V_L$CDR3, wherein the $V_L$ CDR1 comprises an amino acid sequence set forth in SEQ ID NO: 6, $V_L$ CDR2 comprises an amino acid sequence set forth in SEQ ID NO: 7, and $V_L$ CDR3 comprises an amino acid sequence set forth in SEQ ID NO: 8. In some embodiments, the method alleviates one or more symptoms of ectodermal dysplasia 2, Clouston type (OMIM No. 129500) selected from the group consisting of dystrophy of the nails, hypoplasticity and deformation of nails, and increased susceptibility to paronychial infections.

In one aspect, the present technology relates to the treatment, amelioration or prevention of Keratitis-ichthyosis-deafness syndrome (KIDS; OMIM No. 148210) in a subject in need thereof, through administration of therapeutically effective amounts of an antibody or antigen binding fragment thereof comprising a heavy chain immunoglobulin variable domain (VH) and a light chain immunoglobulin variable domain ($V_L$), wherein the $V_H$ comprises complementarity determining regions $V_H$CDR1, $V_H$CDR2 and $V_H$CDR3, wherein the $V_H$ CDR1 comprises an amino acid sequence set forth in SEQ ID NO: 3, $V_H$ CDR2 comprises an amino acid sequence set forth in SEQ ID NO: 4, and $V_H$ CDR3 comprises an amino acid sequence set forth in SEQ ID NO: 5; and wherein the $V_L$ comprises complementarity determining regions $V_L$ CDR1, $V_L$ CDR2 and $V_L$ CDR3, wherein the $V_L$ CDR1 comprises an amino acid sequence set forth in SEQ ID NO: 6, $V_L$ CDR2 comprises an amino acid sequence set forth in SEQ ID NO: 7, and $V_L$ CDR3 comprises an amino acid sequence set forth in SEQ ID NO: 8. In some embodiments, the method alleviates one or more symptoms of KIDS selected from the group consisting of palmoplantar keratoderma, erythrokeratoderma, dry and scaly skin, and hearing loss.

In one aspect, the present technology relates to the treatment, amelioration or prevention of type X Charcot-Marie-Tooth neuropathy (CMTX1; OMIM No. 302800) in a subject in need thereof, through administration of therapeutically effective amounts of an antibody or antigen binding fragment thereof comprising a heavy chain immunoglobulin variable domain (VH) and a light chain immunoglobulin variable domain ($V_L$), wherein the $V_H$ comprises complementarity determining regions $V_H$CDR1, $V_H$CDR2 and $V_H$CDR3, wherein the $V_H$ CDR1 comprises an amino acid sequence set forth in SEQ ID NO: 3, $V_H$ CDR2 comprises an amino acid sequence set forth in SEQ ID NO: 4, and $V_H$CDR3 comprises an amino acid sequence set forth in SEQ ID NO: 5; and wherein the $V_L$ comprises complementarity determining regions $V_L$ CDR1, $V_L$ CDR2 and $V_L$ CDR3, wherein the $V_L$ CDR1 comprises an amino acid sequence set forth in SEQ ID NO: 6, $V_L$ CDR2 comprises an amino acid sequence set forth in SEQ ID NO: 7, and $V_L$ CDR3 comprises an amino acid sequence set forth in SEQ ID NO: 8. In some embodiments, the method alleviates one or more symptoms of CMTX1 selected from the group consisting of loss of muscle tissue, loss of touch sensation, atrophy of muscles in the feet, legs, and hands, or hearing impairment.

In some embodiments, the $V_H$ comprises an amino acid sequence set forth in SEQ ID NO: 11. In some embodiments, the $V_L$ comprises an amino acid sequence set forth in SEQ ID NO: 12.

In some embodiments, the antibody or antigen binding fragment thereof is administered by a route selected from the group consisting of parenteral, oral, inhalation, topical, intraocular, iontophoretic, and transmucosal administration. In some embodiments, the antibody or antigen binding fragment thereof is administered by a parenteral route. In some embodiments, the antibody or antigen binding fragment thereof is administered by a topical route.

In some embodiments, the antibody or antigen binding fragment thereof is an antibody, scFv, $(scFv)_2$, scFv-Fc, Fab, Fab', $F(ab')_2$ or an scFv-Fc antibody. In some embodiments, the antibody or antigen binding fragment thereof is an scFv-Fc antibody. In some embodiments, the scFv-Fc antibody is abEC1.1 or abEC1.1m.

In some embodiments, the antibody or antigen binding fragment thereof is formulated as an ointment, salve, gel, or cream. In some embodiments, the antibody or antigen binding fragment thereof is formulated as an injectable.

BRIEF DESCRIPTION OF THE DRAWINGS

FIGS. 3A-3D display four representative snapshots captured during the simulation, highlighting important interactions. The antibody heavy chain (HC), light chain (LC), and Cx26 protomers (P1-P4) are shown. Each protein is represented according to its realistic volume occupation in space. Critical residues are shown with atomistic detail.

FIG. 7 shows the pharmacokinetics (PK) of abEC1.1 and abEC1.1m antibodies in a wild type mouse strain (C57BL6/N). Serum concentration of the antibodies, as measured by ELISA, are plotted as a function of time following systemic administration at time/=0. Intersection of the dashed lines determines the time (136 h) at which the blood concentration of abEC1.1m falls below 140 nM. Data (mean±s.e.m) were obtained from n=3 humanely euthanized mice per time point; age: from 6 to 8 weeks.

5 cream (50 µg/ml); dose: single application of 100 µl of cream, massaged until completely absorbed in the depilated skin of the mouse back.

Figure 9:
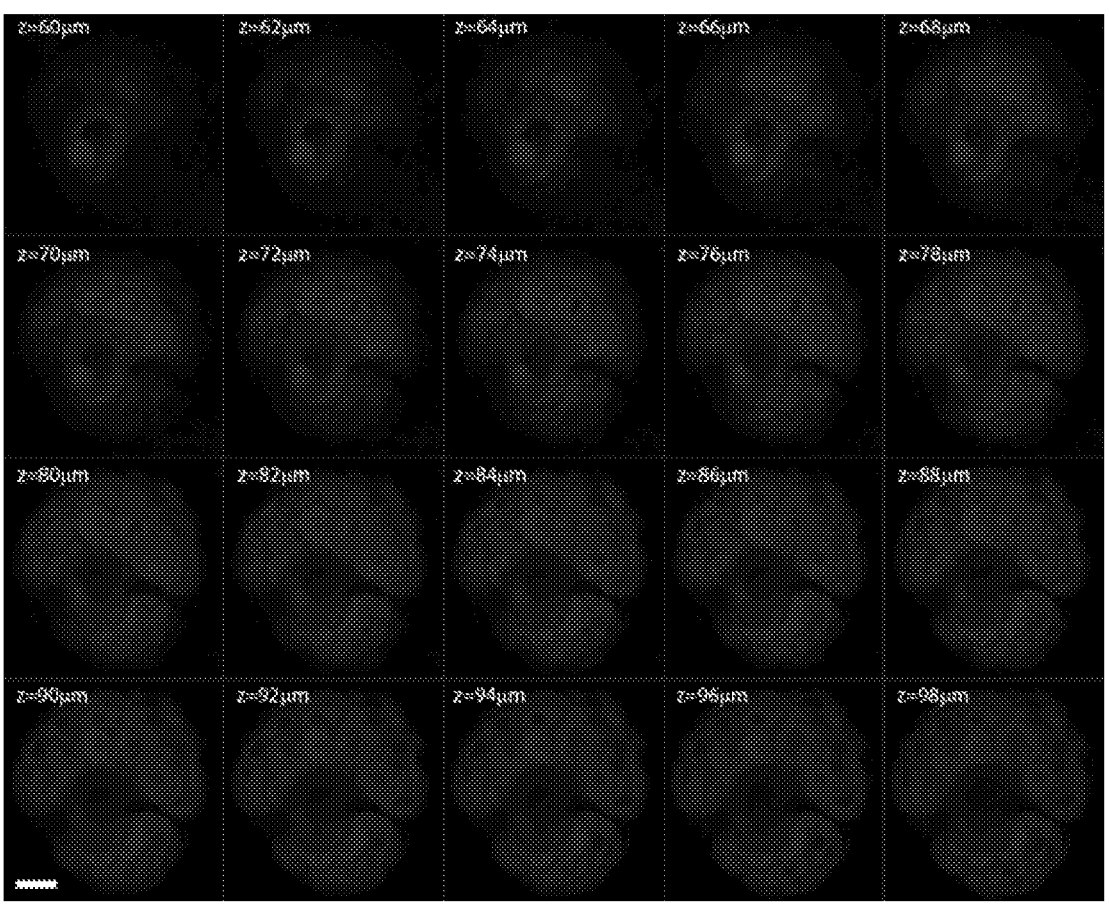

FIG. 9 shows representative confocal microscopy images of a hypertrophic sebaceous gland from an untreated homozygous Cx30A88V mouse (Cx30$^{A88V/A88V}$). Freshly explanted skin sample were stained with Nile red, a marker for intracellular lipids, which detects lipid-filled sebocytes. Provided herein are the images captured at increasing depths from the surface (z=0). Scale bar, 20 µm. To gather these data, the mouse was humanely euthanized, the entire back skin was harvested and skin samples were maintained in short-term culture at the air-medium interface in a Trowell-type system with the stratum corneum of the epidermis exposed to air.

Figure 10:
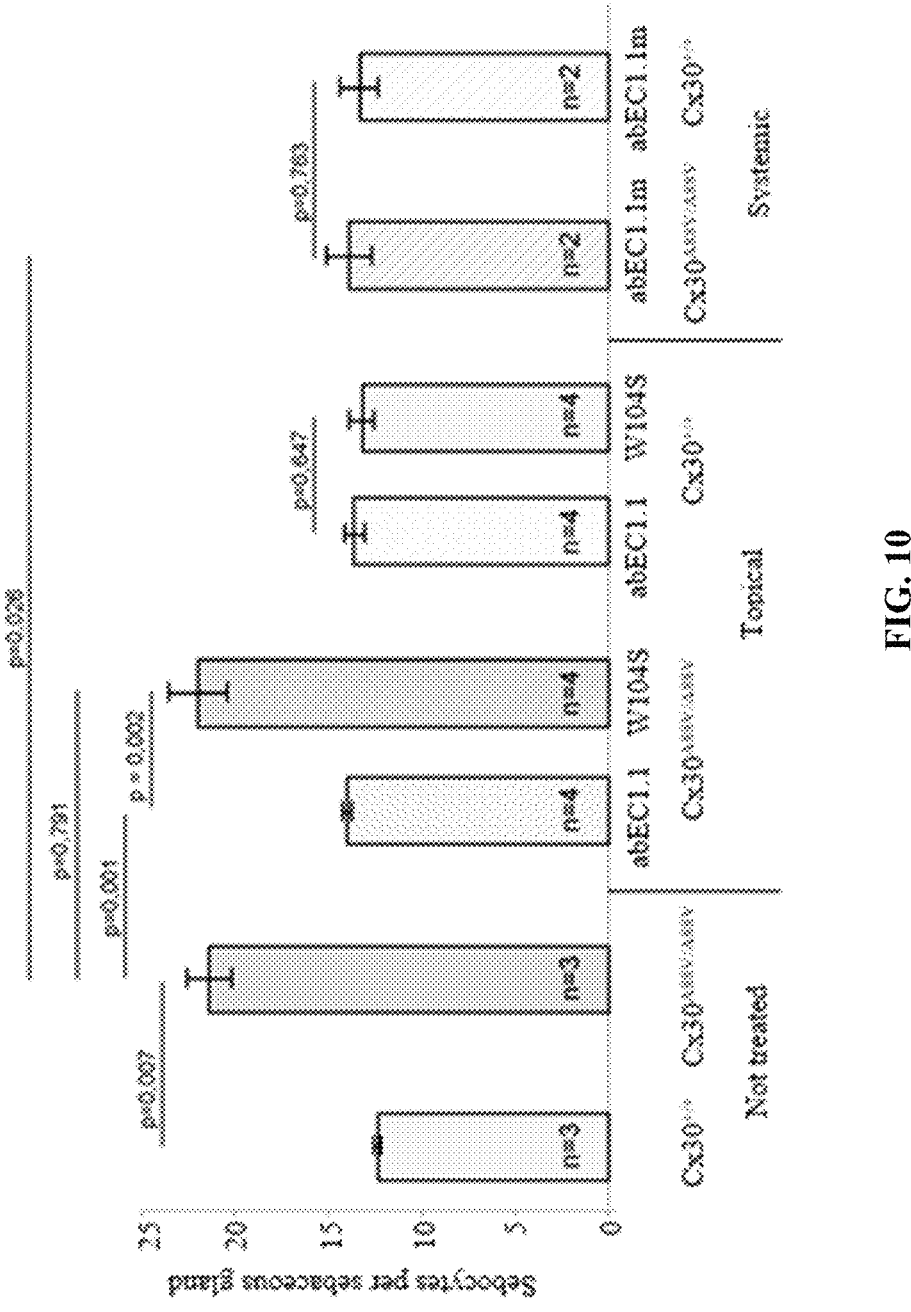

FIG. 10 shows the effect of antibody abEC1.1 on the number of sebocytes in sebaceous glands. Cx30$^{A88V/A88V}$ mice and their wild-type (Cx30$^{+/+}$) littermates were topically treated with vehicle alone, abEC1.1 or W104S, an inactive variant abEC1.1, or systemically with abEC1.1m. Data were obtained by counting of Nile red positive cells, as shown in FIG. 9, in 10-20 sebaceous glands per skin sample. n=number of mice; p=P-value obtained by two-tailed Student's t-test. For topical administration: abEC1.1 cream was rubbed gently onto the left side of the shaved back skin under gas anesthesia (Isofluorane 1.5-2%); the right side was treated with abEC1.1-W104S cream (an internal inactive antibody negative control). Treatment (100 µl cream per side, antibody concentration=50 µg/ml) was repeated daily for two weeks. For Systemic administration: abEC1.1m was delivered via intraperitoneal injection every 3 days with a dose of 10 mg of antibody per kg of mouse weight; intraperitoneal injection treatment was also continued for two weeks.

Figure 11A:
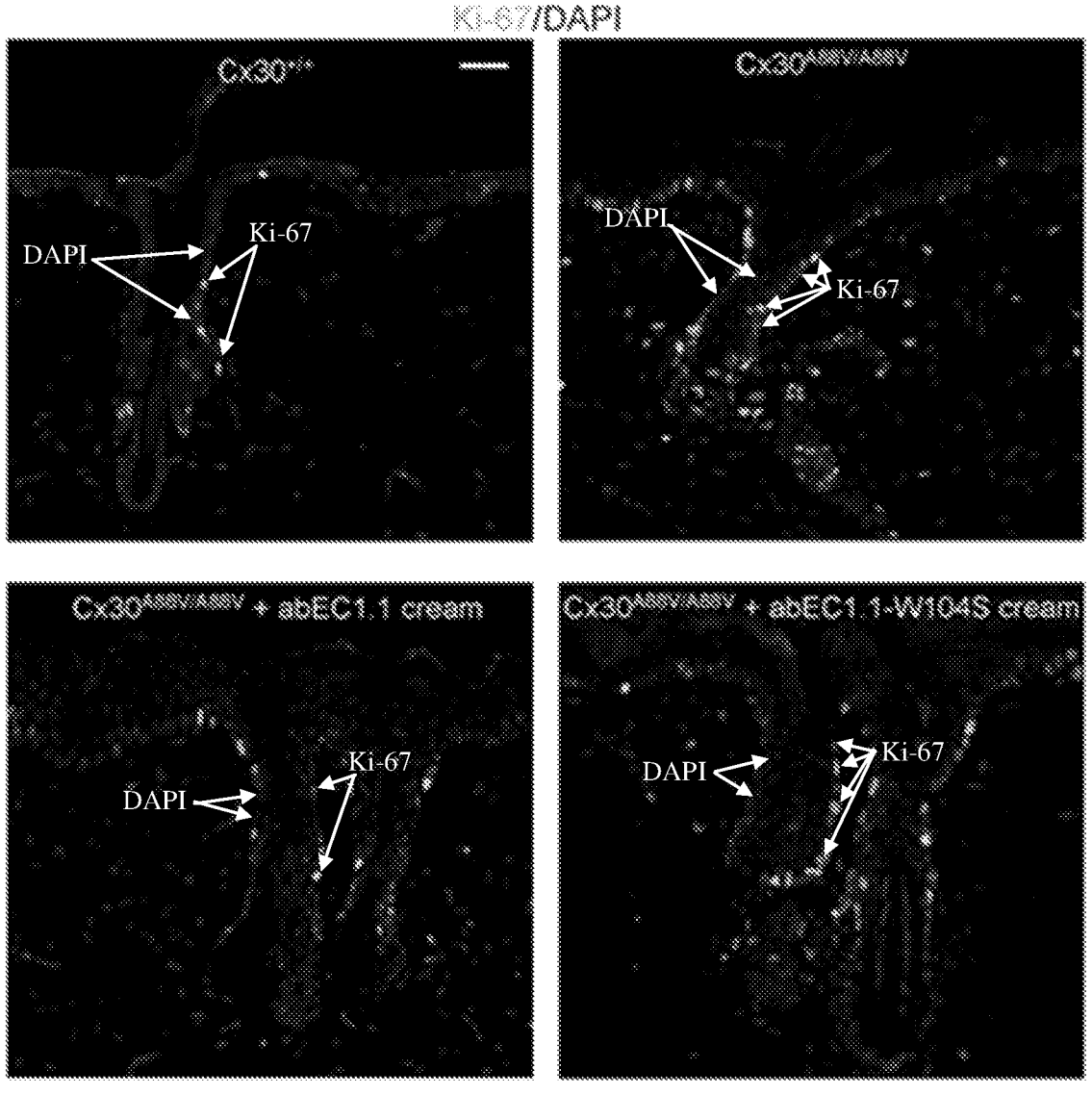
Figure 11:
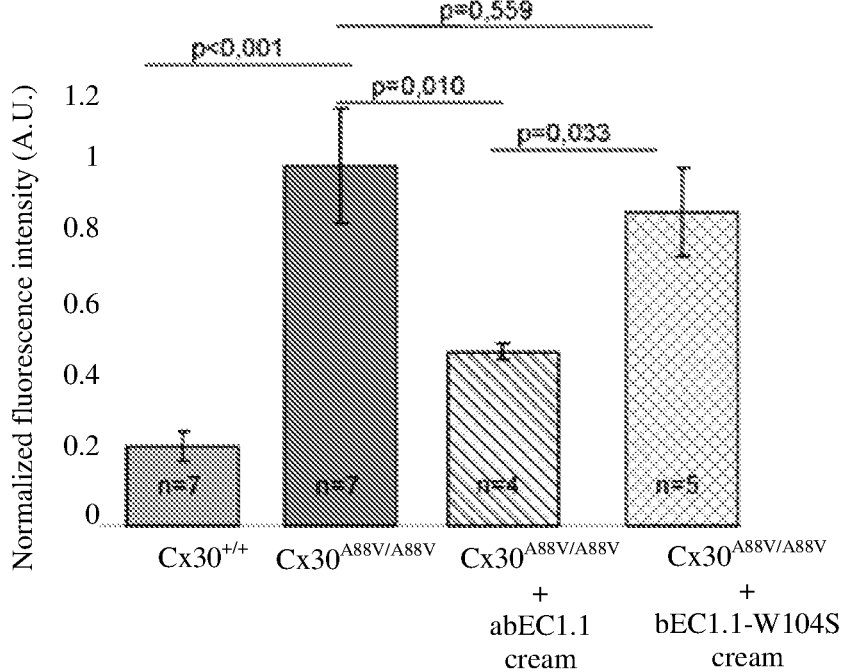

FIG. 11A shows representative transversal sections of mouse dorsal skin showing cells that line the envelope of sebaceous glands labeled with an anti-Ki-67 antibody. Shown are maximal projection renderings of nine consecutive confocal optical sections taken at 1.0 µm intervals; scale bar: 30 µm.

FIG. 11B shows the quantitative analysis of Ki-67 immunoreactivity calculated from the images similar to those displayed in FIG. 11A. n=number of microscope fields of view analyzed, each field=323×323 µm$^2$. p=P-value, two-tailed Student's t-test.

Figure 12:
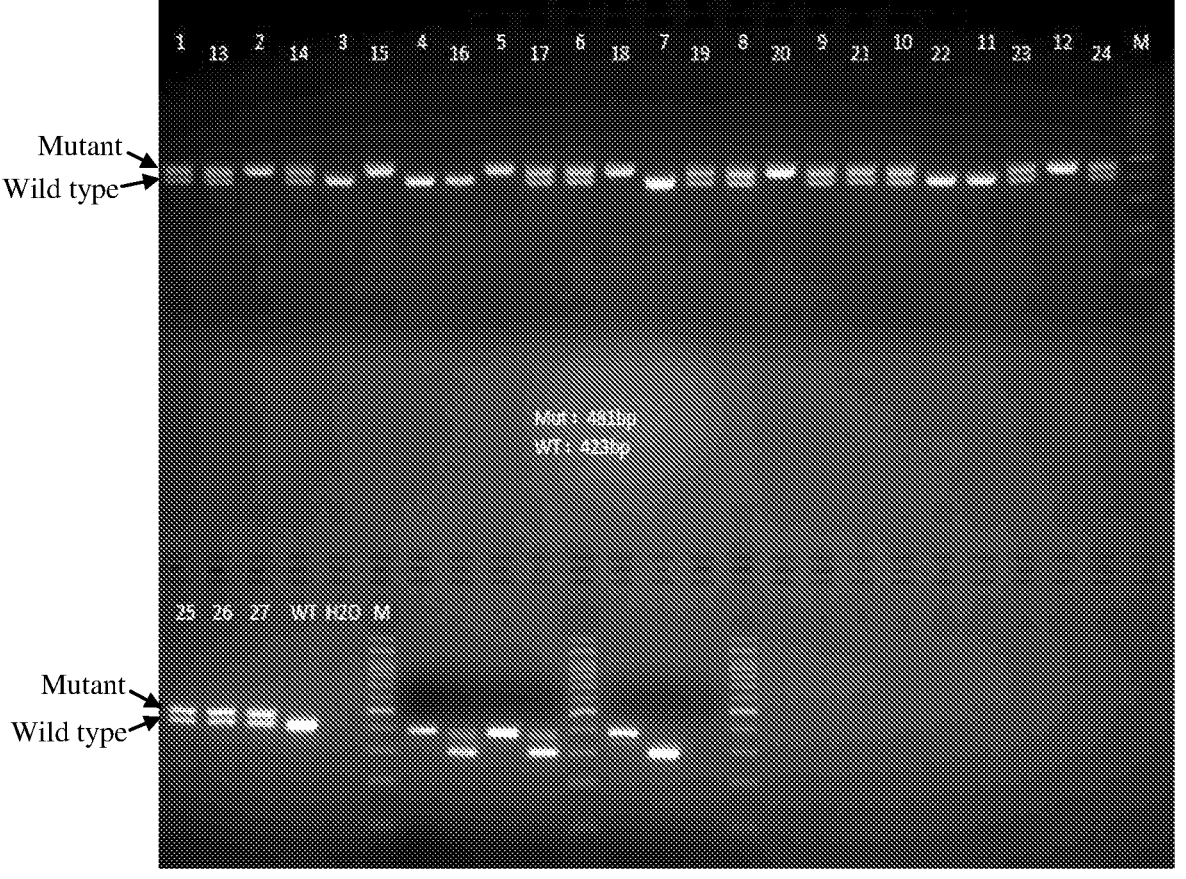

FIG. 12 shows an image of an agarose gel showing the genotyping of Cx30$^{A88V/A88V}$ mice. Genomic DNA samples from wild type, homozygous A88V mutant mice and Cx30$^{+/A88V}$ heterozygous mice were subjected to PCR reactions and analyzed by agarose gel electrophoresis. Locations of the predicted bands at 423 bp for the wild type allele and at 481 bp for the Cx30$^{A88V}$ allele are indicated.

DETAILED DESCRIPTION

It is to be appreciated that certain aspects, modes, embodiments, variations and features of the present technology are described below in various levels of detail in order to provide a substantial understanding of the present technology. The present technology provides methods of treating ectodermal dysplasia 2, Clouston type (OMIM No. 129500), Keratitis-ichthyosis-deafness syndrome (KIDS; OMIM No. 148210), and/or type X Charcot-Marie-Tooth neuropathy (CMTX1; OMIM No. 302800).

While the exemplified antibodies that target the Cx26 hemichannel described herein are scFv-Fc antibodies, the description is intended to embrace broadly to any immunologic binding agent, such as IgG, IgM, IgA, IgD, IgE, and genetically modified IgG, and fragments thereof as well as polypeptides comprising antibody complementarity determining regions (CDR) domains that retain the antigen binding activity described herein.

Definitions

The definitions of certain terms as used in this specification are provided below. Unless defined otherwise, all technical and scientific terms used herein generally have the same meaning as commonly understood by one of ordinary skill in the art to which this present technology belongs.

As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. In some embodiments, the anti-Cx26 antibodies of the present technology is administered by an intracoronary route or an intra-arterial route. Administration includes self-administration and the administration by another.

As used herein, the term "amino acid" is used to refer to any organic molecule that contains at least one amino group and at least one carboxyl group. Typically, at least one amino group is at the α position relative to a carboxyl group. The term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refer to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. As used herein, "antibodies" (includes intact immunoglobulins) and "antigen binding fragments" specifically bind to a molecule of interest (or a group of highly similar molecules of interest) to the substantial exclusion of binding to other molecules (for example, antibodies and antibody fragments that have a binding constant for the molecule of interest that is at least 103 $M^{-1}$ greater, at least $10^4$ $M^{-1}$ greater or at least $10^5$ $M^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., *Immunology*, $3^{rd}$ Ed., W.H. Freeman & Co., New York, 1997.

More particularly, antibody refers to a polypeptide ligand comprising at least a light chain immunoglobulin variable region or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the Vu region and the $V_L$ region are responsible for binding the antigen recognized by the antibody. Typically, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds Cx26 protein will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). "Anti-Cx26 antibodies of the present technology" as used herein, refers to antibodies (including monoclonal antibodies, polyclonal antibodies, humanized antibodies, chimeric antibodies, recombinant antibodies, multispecific antibodies, bispecific antibodies, etc.,) as well as antibody fragments. An antibody or antigen binding fragment thereof specifically binds to an antigen.

As used herein, the term "antibody-related polypeptide" means antigen-binding antibody fragments, including single-chain antibodies, that can comprise the variable region(s) alone, or in combination, with all or part of the following polypeptide elements: hinge region, $CH_1$, $CH_2$, and $CH_3$ domains of an antibody molecule. Also included in the technology are any combinations of variable region(s) and hinge region, $CH_1$, $CH_2$, and $CH_3$ domains. Antibody-related molecules useful in the present methods, e.g., but are not limited to, Fab, Fab' and $F(ab')_2$, Fd, single-chain Fvs (scFv), single-chain antibodies, disulfide-linked Fvs (sdFv) and fragments comprising either a $V_L$ or $V_H$ domain. Examples include: (i) a Fab fragment, a monovalent fragment consisting of the $V_L$, $V_H$, $C_L$ and $CH_1$ domains; (ii) a $F(ab')_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., *Nature* 341:544-546, 1989), which consists of a $V_H$ domain; and (vi) an isolated complementarity determining region (CDR). As such "antibody fragments" or "antigen binding fragments" can comprise a portion of a full length antibody, generally the antigen binding or variable region thereof. Examples of antibody fragments or antigen binding fragments include Fab, Fab', $F(ab')_2$, and Fv fragments; diabodies; linear antibodies; single-chain antibody molecules; and multispecific antibodies formed from antibody fragments.

As used herein, the term "conjugated" refers to the association of two molecules by any method known to those in the art. Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking.

As used herein, the term "diabodies" refers to small antibody fragments with two antigen-binding sites, which fragments comprise a heavy-chain variable domain ($V_H$) connected to a light-chain variable domain ($V_L$) in the same polypeptide chain ($V_H$$V_L$). By using a linker that is too short to allow pairing between the two domains on the same chain, the domains are forced to pair with the complementary domains of another chain and create two antigen binding sites. Diabodies are described more fully in, e.g., EP 404, 097; WO 93/11161; and Hollinger et al., *Proc. Natl. Acad. Sci. USA*, 90:6444-6448 (1993).

As used herein, the terms "single-chain antibodies" or "single-chain Fv (scFv)" refer to an antibody fusion molecule of the two domains of the Fv fragment, $V_L$ and $V_H$. Single-chain antibody molecules may comprise a polymer with a number of individual molecules, for example, dimer, trimer or other polymers. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single-chain Fv (scFv)). Bird et al. (1988) *Science* 242:423-426 and Huston et al. (1988) *Proc. Natl. Acad Sci*. USA 85:5879-5883. Such single-chain antibodies can be prepared by recombinant techniques or enzymatic or chemical cleavage of intact antibodies.

As used herein, an "antigen" refers to a molecule to which an antibody (or antigen binding fragment thereof) can selectively bind. The target antigen may be a protein, carbohydrate, nucleic acid, lipid, hapten, or other naturally occurring or synthetic compound. In some embodiments, the target antigen may be a polypeptide (e.g., a Cx26 hemichannel polypeptide, or one or two extracellular loops (EC1 and/or EC2)). An antigen may also be administered to an animal to generate an immune response in the animal.

The term "antigen binding fragment" refers to a fragment of the whole immunoglobulin structure which possesses a part of a polypeptide responsible for binding to antigen. Examples of the antigen binding fragment useful in the present technology include scFv, (scFv)$_2$, scFv-Fc, Fab, Fab' and F(ab')$_2$, but are not limited thereto.

Any of the above-noted antibody fragments are obtained using conventional techniques known to those of skill in the art, and the fragments are screened for binding specificity and neutralization activity in the same manner as are intact antibodies.

By "binding affinity" is meant the strength of the total noncovalent interactions between a single binding site of a molecule (e.g., an antibody) and its binding partner (e.g., an antigen or antigenic peptide). The affinity of a molecule X for its partner Y can generally be represented by the dissociation constant (KD). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

As used herein, the term "biological sample" means sample material derived from living cells. Biological samples may include tissues, cells, protein or membrane extracts of cells, and biological fluids (e.g., ascites fluid or cerebrospinal fluid (CSF)) isolated from a subject, as well as tissues, cells and fluids present within a subject. Biological samples of the present technology include, but are not limited to, samples taken from breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, thymus, blood, hair, buccal, skin, serum, plasma, CSF, semen, prostate fluid, seminal fluid, urine, feces, sweat, saliva, sputum, mucus, bone marrow, lymph, and tears. Biological samples can also be obtained from biopsies of internal organs or from cancers. Biological samples can be obtained from subjects for diagnosis or research or can be obtained from non-diseased individuals, as controls or for basic research. Samples may be obtained by standard methods including, e.g., venous puncture and surgical biopsy. In certain embodiments, the biological sample is a skin tissue, hair, nails, sebaceous glands, or a muscle biopsy sample.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, a "connexin," also known as "gap junction proteins" means a member of a family of tetratransmembrane proteins. The human genome contains about twenty genes that encode distinct but structurally related connexin isoforms, which exhibit complex developmental and tissue-restricted patterns of expression. Most tissues express multiple connexin types and individual isoforms can assemble into homo- and/or hetero-hexameric complexes called the hemichannels.

As used herein, a "hemichannel" or a connexon" means the structures composed of homo- or heterohexameric arrays connexins. Hemichannels either remain unpaired at the cell surface, or dock with their counterparts in adjacent cells to form intercellular gap junction channels. Gap junction channels allow for the passage of small molecules between cells, playing key roles in embryonic development, tissue homeostasis, and response to pathologic stress. Without wishing to be bound by theory, several pathological condition are thought to occur when mutant connexins form homo- or heterohexameric arrays with co-expressed wild type connexins leading to transdominant effects that result in mutant gap junction channels.

Under physiological conditions, connexin (Cx) hemichannels are mostly closed. They open under certain stimuli, such as cell plasma membrane depolarization and/or lowering of extracellular $Ca^{2+}$ concentration, allowing the release of autocrine and paracrine molecules. Some mutations in connexin genes lead to the formation of mutant hemichannels associated with human diseases, including ectodermal dysplasia 2, Clouston type (OMIM No. 129500), Keratitis-ichthyosis-deafness syndrome (KIDS; OMIM No. 148210), and/or type X Charcot-Marie-Tooth neuropathy (CMTX1; OMIM No. 302800).

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

An "isolated" or "purified" polypeptide or peptide is substantially free of cellular material or other contaminating polypeptides from the cell or tissue source from which the agent is derived, or substantially free from chemical precursors or other chemicals when chemically synthesized. For example, isolated anti-Cx26 antibodies of the present technology would be free of materials that would interfere with diagnostic or therapeutic uses of the agent. Such interfering materials may include enzymes, hormones and other proteinaceous and nonproteinaceous solutes.

As used herein, the term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. In some embodiments, an "epitope" of the a Cx26 hemichannel is a region of the protein to which the anti-Cx30 antibodies of the present technology specifically bind, including one or two extracellular loops (EC1 and/or EC2). In some embodiments, the epitope is a conformational epitope or a nonconformational epitope. To screen for anti-Cx30 antibodies which bind to an epitope, a routine cross-blocking assay such as that described in Antibodies, A Laboratory Manual, Cold Spring Harbor Laboratory, Ed Harlow and David Lane (1988), can be performed. This assay can be used to determine if an anti-Cx30 antibody binds the same site or epitope as an anti-Cx30 antibody of the present technology. Alternatively, or additionally, epitope mapping can be performed by methods known in the art. For example, the antibody sequence can be mutagenized such as by alanine scanning, to identify contact residues. In a different method, peptides corresponding to different regions of Cx30 protein can be used in competition assays with the test antibodies or with a test antibody and an antibody with a characterized or known epitope.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

As used herein, the terms "Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, "humanized" forms of non-human (e.g., murine) antibodies are chimeric antibodies which contain minimal sequence derived from non-human immunoglobulin. For the most part, humanized antibodies are human immunoglobulins in which hypervariable region residues of the recipient are replaced by hypervariable region residues from a non-human species (donor antibody) such as mouse, rat, rabbit or nonhuman primate having the desired specificity, affinity, and capacity. In some embodiments, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains (e.g., Fab, Fab', $F(ab')_2$, or Fv), in which all or substantially all of the hypervariable loops correspond to those of a non-human immunoglobulin and all or substantially all of the FR regions are those of a human immunoglobulin consensus FR sequence although the FR regions may include one or more amino acid substitutions that improve binding affinity. The number of these amino acid substitutions in the FR are typically no more than 6 in the H chain, and in the L chain, no more than 3. The humanized antibody optionally may also comprise at least a portion of an immunoglobulin constant region (Fc), typically that of a human immunoglobulin. For further details, see Jones et al., *Nature* 321: 522-525 (1986); Riechmann et al., *Nature* 332:323-327 (1988); and Presta, *Curr. Op. Struct. Biol.* 2:593-596 (1992). See e.g., Ahmed & Cheung, *FEBS Letters* 588 (2): 288-297 (2014); Saxena & Wu, *Frontiers in immunology* 7:580 (2016).

As used herein, the terms "identical" or percent "identity", when used in the context of two or more nucleic acids or polypeptide sequences, refer to two or more sequences or subsequences that are the same or have a specified percentage of amino acid residues or nucleotides that are the same (i.e., about 60%, 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein)), when compared and aligned for maximum correspondence over a comparison window or designated region as measured using a BLAST or BLAST 2.0 sequence comparison algorithms with default parameters described below, or by manual alignment and visual inspection (e.g., NCBI web site). Such sequences are then said to be "substantially identical." This term also refers to, or can be applied to, the complement of a test sequence. The term also includes sequences that have deletions and/or additions, as well as those that have substitutions. In some embodiments, identity exists over a region that is at least about 25 amino acids or nucleotides in length, or 50-100 amino acids or nucleotides in length.

As used herein, the term "intact antibody" or "intact immunoglobulin" means an antibody that has at least two heavy (H) chain polypeptides and two light (L) chain polypeptides interconnected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: $FR_1$, $CDR_1$, $FR_2$, $CDR_2$, $FR_3$, $CDR_3$, $FR_4$. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

As used herein, the terms "individual", "patient", or "subject" can be an individual organism, a vertebrate, a mammal, or a human. In some embodiments, the individual, patient or subject is a human.

The term "monoclonal antibody" as used herein refers to an antibody obtained from a population of substantially homogeneous antibodies, i.e., the individual antibodies comprising the population are identical except for possible naturally occurring mutations that may be present in minor amounts. For example, a monoclonal antibody can be an antibody that is derived from a single clone, including any eukaryotic, prokaryotic, or phage clone, and not the method by which it is produced. A monoclonal antibody composition displays a single binding specificity and affinity for a particular epitope. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. Monoclonal antibodies can be prepared using a wide variety of techniques known in the art including, e.g., but not limited to, hybridoma, recombinant, and phage display technologies. For example, the monoclonal antibodies to be used in accordance with the present methods may be made by the hybridoma method first described by Kohler et al., *Nature* 256:495 (1975), or may be made by recombinant DNA methods (See, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences (20$^{th}$ edition, ed. A. Gennaro, 2000, Lippincott, Williams & Wilkins, Philadelphia, PA.).

As used herein, "prevention" or "preventing" of a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, "specifically binds" refers to a molecule (e.g., an antibody or antigen binding fragment thereof) which recognizes and binds another molecule (e.g., an antigen), but that does not substantially recognize and bind other molecules. The terms "specific binding," "specifically binds to," or is "specific for" a particular molecule (e.g., a polypeptide, or an epitope on a polypeptide), as used herein, can be exhibited, for example, by a molecule having a KD for the molecule to which it binds to of about $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M. The term "specifically binds" may also refer to binding where a molecule (e.g., an antibody or antigen binding fragment thereof) binds to a particular polypeptide (e.g., a Cx26 polypeptide), or an epitope on a particular polypeptide, without substantially binding to any other polypeptide, or polypeptide epitope.

As used herein, the terms "subject," "individual," or "patient" can be an individual organism, a vertebrate, a mammal, or a human.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for ectodermal dysplasia 2, Clouston type (OMIM No. 129500), Keratitis-ichthyosis-deafness syndrome (KIDS; OMIM No. 148210), and/or type X Charcot-Marie-Tooth neuropathy (CMTX1; OMIM No. 302800), if, after receiving a therapeutic amount of the anti-Cx26 antibodies of the present technology according to the methods described herein, the subject shows observable and/or measurable restoration of the function of the mutant connexin hemichannel. It is also to be appreciated that the various modes of treatment or prevention of medical conditions as described are intended to mean "substantial", which includes total but also less than total treatment or prevention, and wherein some biologically or medically relevant result is achieved.

It is also to be appreciated that the various modes of treatment of disorders as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Amino acid sequence modification(s) of the anti-connexin Cx26 hemichannel antibodies described herein are contemplated. For example, it may be desirable to improve the binding affinity and/or other biological properties of the antibody. Amino acid sequence variants of an anti-connexin Cx26 hemichannel antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to obtain the antibody of interest, as long as the obtained antibody possesses the desired properties. The modification also includes the change of the pattern of glycosylation of the protein. The sites of greatest interest for substitutional mutagenesis include the hypervariable regions, but FR alterations are also contemplated. "Conservative substitutions" are shown in the Table below.

| Amino Acid Substitutions | | |
|---|---|---|
| Original Residue | Exemplary Substitutions | Conservative Substitutions |
| Ala (A) | val, leu, ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

One type of substitutional variant involves substituting one or more hypervariable region residues of a parent antibody. A convenient way for generating such substitutional variants involves affinity maturation using phage display. Specifically, several hypervariable region sites (e.g., 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen. Such contact residues and neighboring residues are candidates for substitution according to the techniques elaborated herein. Once such variants are generated, the panel of variants is subjected to screening as described herein and antibodies with similar or superior properties in one or more relevant assays may be selected for further development.

Pathogenesis of Clouston Syndrome

Ectodermal dysplasia (ED) is a diverse group of genetic disorders exhibiting abnormalities in skin, sweat glands, hair, nails, teeth and/or mucous membranes. Usually at least two organs are affected, and each combination is considered a distinct type of ED. Clouston Syndrome (also known as autosomal dominant Clouston hidrotic ectodermal dysplasia; ectodermal dysplasia 2, Clouston type; OMIM No. 129500) affects the hair and nails.

Clouston Syndrome is a single gene genodermatosis characterized by dystrophy of the nails that tend to be hypoplastic and deformed with increased susceptibility to paronychial infections. Defects of the hair that range from brittleness and slow growth rate to total alopecia, and moderate to severe palmoplantar hyperkeratosis with reduced keratinocyte desquamation. Sensorineural hearing loss has also been reported in some cases. There is a lot of variability between patients with respect to the time of onset as well as severity of symptoms. Clouston syndrome is caused by mutations in the GJB6 gene, which encodes the gap junction beta 1 protein (connexin 30). A sub-set of these mutations (G11R, A88V), generate hemichannels with augmented activity in the cell plasma membrane.

Pathogenesis of Keratitis-Ichthyosis-Deafness (KID)

Keratitis-ichthyosis-deafness (KID) syndrome is a hereditary condition that causes skin abnormalities, eye problems, and hearing loss. KID syndrome is present from birth. Nearly all affected individuals have skin involvement and sensorineural deafness or severe hearing impairment. Skin symptoms include palmoplantar keratoderma (thick, hard skin on the underside of the hands and feet), erythrokeratoderma (red patches), and dry, scaly skin. Hearing loss is usually severe. KID syndrome is caused by mutations in the GJB2 gene, which codes for the gap junction beta 2 (connexin 26). A sub-set of these mutations (G12R, N14K, D50N, N14Y, S17F, A40V, G45E, D50A, A88V) generate hemichannels with augmented activity in the cell plasma membrane.

Pathogenesis of Charcot-Marie-Tooth Neuropathy

Charcot-Marie-Tooth neuropathy is a group of hereditary disorders that are characterized by damage to the peripheral nerves. Peripheral nerves connect the brain and spinal cord to muscles and to sensory cells that detect sensations such as touch, pain, heat, and sound. Damage to the peripheral nerves that worsens over time, which results in progressive loss of muscle tissue and touch sensation across various parts of the body, wasting (atrophy) of muscles in the feet, legs, and hands.

There are several types of Charcot-Marie-Tooth disease, which are differentiated by their effects on nerve cells and patterns of inheritance. Type X Charcot-Marie-Tooth disease (CMTX) is caused by mutations in genes on the X chromosome, one of the two sex chromosomes. Due to its X-linked inheritance pattern, CMTX affects males more severely than females. CMTX is caused by mutations in the GJB1 gene located on the X-chromosome, which encodes for a protein called connexin-32 (also known as gap junction beta 1). A sub-set of these mutations (S85C, D178Y, F235C) generate hemichannels with augmented activity in the cell plasma membrane.

Anti-Cx26 Antibodies of the Present Technology

The present technology describes methods and compositions for the generation and use of anti-Cx26 antibodies of the present technology (e.g., anti-Cx26 antibodies or antigen binding fragments thereof). The anti-Cx26 antibodies of the The scFv-Fc antibody abEC1.1 was selected out of a vast human scFv phage library based on inhibition of homomeric hemichannels composed of human connexin 26 (hCx26) protomers. WO2017/128880. The crystal structure of the scFv domain of abEC1.1 was solved, and the amino acid residues that are critical for binding to Cx26 were identified.

The Table below shows the amino acid sequences of extracellular loops (EC1 and EC2) of wild type Cx26 protein, which mediate binding of the antibody to its antigen (connexin hemichannel).

| Sequence Identifier | Description | Residue numbers |
|---|---|---|
| SEQ ID NO: 1 | NTLQP | 54-58 (EC1) |
| SEQ ID NO: 2 | PN | 175-176 (EC2) |

The Table below provides antibody-related sequences, including the complementarity determining region (CDR):

| SequenceId entifier | Description | Sequence |
|---|---|---|
| SEQ ID NO: 3 | abEC1.1 $V_H$ CDR1 | GFTFSSYA |
| SEQ ID NO: 4 | abEC1.1 $V_H$ CDR2 | ISHGGSNNK |
| SEQ ID NO: 5 | abEC1.1 $V_H$ CDR3 | ARDFSWRGYYMDV |
| SEQ ID NO: 6 | abEC1.1 $V_L$ CDR1 | QSISSY |
| SEQ ID NO: 7 | abEC1.1 $V_L$ CDR2 | GAS |
| SEQ ID NO: 8 | abEC1.1 $V_L$ CDR3 | QQYGSSPRT |
| SEQ ID NO: 9 | abEC1.1 VH DNA | CAGGTACAGCTGCAGCAGTCAGGGGGGGGCGTGGTCCAGCC TGGGAGGTCCCTGAGACTCTCCTGTGCAGCCTCTGGATTCA CCTTCAGTAGCTATGCTATGCACTGGGTCCGCCAGGCTCCA GGCAAGGGGCTGGAGTGGGTGGCAGTTATATCACATGGTGG AAGTAATAAATACTACGCAGACTCCGTGAAGGGCCGATTCA CCATCTCCAGAGACAATTCCAAGAACACGCTGTATCTGCAA ATGAACAGCCTGAGAGCTGAGGACACGGCTGTGTATTACTG TGCGAGAGATTTTAGTTGGAGAGGGTACTACATGGACGTCT GGGGCAAAGGCACCCTGGTCACCGTCTCCTCA |
| SEQ ID NO: 10 | abEC1.1 VL DNA | GAAACGACACTCACGCAGTCTCCAGCCACCCTGTCTTTGTC TCCAGGGGAAAGAGCCACCCTCTCCTGCAGGGCCAGTCAGA GTATTAGCAGCTACTTAGCCTGGTACCAGCAGAAACCTGGC CAGGCTCCCAGGCTCCTCATCTATGGTGCATCCACCAGGGC CACTGGCATCCCAGACAGGTTCAGTGGCAGTGGGTCTGGGA CAGACTTCACTCTCACCATCAGCAGACTGGAGCCTGAAGAT TTTGCAGTGTATTACTGTCAGCAGTATGGTAGCTCACCTCG AACTTTCGGCGGAGGGACCAAGGTGGAAATCAAACGT |
| SEQ ID NO: 11 | abEC1.1 VH Por | QVQLQQSGGGVVQPGRSLRLSCAASGFTFSSYAMHWVRQAP GKGLEWVAVISHGGSNKYYADSVKGRFTISRDNSKNTLYLQ MNSLRAEDTAVYYCARDFSWRGYYMDVWGKGTLVTVSS |
| SEQ ID NO: 12 | abEC1.1 VL Pro | ETTLTQSPATLSLSPGERATLSCRASQSISSYLAWYQQKPG QAPRLLIYGASTRATGIPDRFSGSGSGTDFTLTISRLEPED FAVYYCQQYGSSPRTFGGGTKVEIKR | present technology may be useful in the diagnosis, or treatment of ectodermal dysplasia 2, Clouston type (OMIM No. 129500), Keratitis-ichthyosis-deafness syndrome (KIDS; OMIM No. 148210), and/or type X Charcot-Marie-Tooth neuropathy (CMTX1; OMIM No. 302800). Anti-Cx26 antibodies of the present technology within the scope of the present technology include, e.g., but are not limited to, monoclonal, chimeric, humanized, bispecific antibodies and diabodies that specifically bind the target polypeptide, a homolog, derivative or a fragment thereof.

Accordingly, the antibody or antigen binding fragment thereof (anti-Cx26 antibodies of the present technology) may comprise a heavy chain immunoglobulin variable domain ($V_H$) and a light chain immunoglobulin variable domain ($V_L$), wherein the $V_H$ comprises complementarity determining regions $V_H$ CDR1, $V_H$ CDR2 and $V_H$ CDR3, wherein the $V_H$ CDR1 comprises an amino acid sequence set forth in SEQ ID NO: 3, $V_H$ CDR2 comprises an amino acid sequence set forth in SEQ ID NO: 4, and $V_H$ CDR3 comprises an amino acid sequence set forth in SEQ ID NO:

5; and wherein the $V_L$ comprises complementarity determining regions $V_L$ CDR1, $V_L$ CDR2 and $V_L$ CDR3, wherein the $V_L$ CDR1 comprises an amino acid sequence set forth in SEQ ID NO: 6, $V_L$ CDR2 comprises an amino acid sequence set forth in SEQ ID NO: 7, and $V_L$ CDR3 comprises an amino acid sequence set forth in SEQ ID NO: 8. In some embodiments, the $V_H$ comprises an amino acid sequence set forth in SEQ ID NO: 11. In some embodiments, the $V_L$ comprises an amino acid sequence set forth in SEQ ID NO: 12. In some embodiments, the $V_H$ is encoded by a nucleic acid sequence set forth in SEQ ID NO: 9. In some embodiments, the $V_L$ is encoded by a nucleic acid sequence set forth in SEQ ID NO: 10.

The antibody or antigen binding fragment thereof (anti-Cx26 antibodies of the present technology) may specifically bind to the extracellular loops EC1 and/or EC2 of connexin 26 (Cx26), connexin 32 (Cx32), connexin 30 (Cx30) or a mutant thereof. In some embodiments, the EC1 comprises a sequence set forth in SEQ ID NO: 1 (NTLQP). In some embodiments, the EC2 comprises a sequence set forth in SEQ ID NO: 2 (PN). In some embodiments, anti-Cx26 antibodies of the present technology inhibits formation of a gap junction by binding to a hemichannel. In some embodiments, anti-Cx26 antibodies of the present technology prevent cell death or dysfunction by reducing or blocking the transfer of ions and molecules across the cells plasma membrane through mutant connexin hemichannels with augmented activity. In some embodiments, anti-Cx26 antibodies of the present technology prevent cell death or dysfunction by restoring the function of mutant connexin hemichannels.

In some embodiments, the antibody or antigen binding fragment thereof is an antibody, scFv, (scFv) 2, scFv-Fc, Fab, Fab', F(ab')$_2$ or an scFv-Fc antibody. In some embodiments, the antibody or antigen binding fragment thereof is an scFv-Fc antibody. In some embodiments, the scFv-Fc antibody is abEC1.1 or abEC1.1m.

Formulations

By way of an example, anti-Cx26 antibodies of the present technology is formulated in a simple delivery vehicle. However, anti-Cx26 antibodies of the present technology may be lyophilized or incorporated in a gel, cream, biomaterial, sustained release delivery vehicle.

Anti-Cx26 antibodies of the present technology are generally combined with a pharmaceutically acceptable carrier. The term "pharmaceutically acceptable carrier" refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids and amino acid copolymers. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles. Pharmaceutically acceptable salts can also be present in the pharmaceutical composition, e.g. mineral acid salts such as hydrochlorides, hydrobromides, phosphates, sulfates, and the like; and the salts of organic acids such as acetates, propionates, malonates, benzoates, and the like.

The anti-Cx26 antibodies of the present technology may be provided in the form of a dressing. That is to say, anti-Cx26 antibodies of the present technology is provided in the form of a liquid, semi-solid or solid composition for application directly to the skin surface, or the composition is applied to the surface of, or incorporated into, a solid skin contacting layer such as a dressing gauze or film. The dressing composition may be provided in the form of a fluid or a gel. The anti-Cx26 antibodies of the present technology may be provided in combination with conventional pharmaceutical excipients for topical application to a wound. Suitable carriers include: Hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (Carbopols). Suitable carriers also include creams/ointments used for topical pharmaceutical preparations, e.g. creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilisers such as EDTA.

In some embodiments, the wound dressing composition may be a slow release solid composition, in which the at least one anti-Cx26 antibodies of the present technology is dispersed in a slow release solid matrix such as a matrix of alginate, collagen, or a synthetic bioabsorbable polymer. Preferably, the dressing composition is sterile. The term "dressing" in this specification refers to a dressing for topical application to skin. For example, the anti-Cx26 antibodies of the present technology may be dispersed in or on a solid sheet of skin contacting material such as a woven or nonwoven textile material, or may be dispersed in a layer of foam such as polyurethane foam, or in a hydrogel such as a polyurethane hydrogel, a polyacrylate hydrogel, gelatin, carboxymethyl cellulose, pectin, alginate, and/or hyaluronic acid hydrogel, for example in a gel or ointment. In some embodiments the anti-Cx26 antibodies of the present technology is dispersed in or on a biodegradable sheet material that provides sustained release of the active ingredient into the wound, for example a sheet of freeze-dried collagen, freeze-dried collagen/alginate mixtures (available under the Registered Trade Mark FIBRACOL from Johnson & Johnson Medical Limited) or freeze-dried collagen/oxidized regenerated cellulose (available under the Registered Trade Mark PROMOGRAN from Johnson & Johnson Medical Limited).

In some embodiments, the antibody or antigen binding fragment thereof is formulated as an ointment, salve, gel, or cream. In some embodiments, the antibody or antigen binding fragment thereof is formulated as an injectable.

Modes of Administration and Effective Dosages

Any method known to those in the art for contacting a cell, organ or tissue with a peptide may be employed. Suitable methods include in vitro, ex vivo, or in vivo methods. In vivo methods typically include the administration of an anti-Cx26 antibodies of the present technology, such as those described above, to a mammal, suitably a human. When used in vivo for therapy, the anti-Cx26 antibodies of the present technology are administered to the subject in effective amounts (i.e., amounts that have desired therapeutic effect). The dose and dosage regimen will depend upon the degree of the infection in the subject, the characteristics of the particular anti-Cx26 antibodies of the present technology used, e.g., its therapeutic index, the subject, and the subject's history.

The effective amount may be determined during preclinical trials and clinical trials by methods familiar to physicians and clinicians. An effective amount of a peptide useful in the methods may be administered to a mammal in need thereof by any of a number of well-known methods for administering pharmaceutical compounds. The peptide may be administered systemically or locally.

The anti-Cx26 antibodies of the present technology described herein can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, anti-bacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

In some embodiments, the anti-Cx26 antibodies of the present technology is administered by a parenteral route. In some embodiments, the antibody or antigen binding fragment thereof is administered by a topical route.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The anti-Cx26 antibodies of the present technology compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and anti-fungal agents, for example, parabens, chlorobutanol, phenol, ascorbic acid, thiomerasol, and the like. Glutathione and other antioxidants can be included to prevent oxidation. In many cases, isotonic agents are included, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the anti-Cx26 antibodies of the present technology can be delivered in the form of an aerosol spray from a pressurized container or dispenser which contains a suitable propellant, e.g., a gas such as carbon dioxide, or a nebulizer. Such methods include those described in U.S. Pat. No. 6,468,798.

Systemic administration of an anti-Cx26 antibodies of the present technology as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

An anti-Cx26 antibodies of the present technology can be formulated in a carrier system. The carrier can be a colloidal system. The colloidal system can be a liposome, a phospholipid bilayer vehicle. In one embodiment, the therapeutic peptide is encapsulated in a liposome while maintaining peptide integrity. As one skilled in the art would appreciate, there are a variety of methods to prepare liposomes. (See Lichtenberg et al., *Methods Biochem. Anal.*, 33:337-462 (1988); Anselem et al., *Liposome Technology*, CRC Press (1993)). Liposomal formulations can delay clearance and increase cellular uptake (See Reddy, *Ann. Pharmacother.,* 34 (7-8): 915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the anti-Cx26 antibodies of the present technology can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.,* 34 (7-8): 915-923 (2000)). A polymer formulation for human growth hormone (hGH) has been used in clinical trials. (See Kozarich and Rich, *Chemical Biology,* 2:548-552 (1998)).

Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the anti-Cx26 antibodies of the present technology are prepared with carriers that will protect the anti-Cx26 antibodies of the present technology against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The anti-Cx26 antibodies of the present technology can also be formulated to enhance intracellular delivery. For example, liposomal delivery systems are known in the art, see, e.g., Chonn and Cullis, "Recent Advances in Liposome Drug Delivery Systems," Current Opinion in Biotechnology 6:698-708 (1995); Weiner, "Liposomes for Protein Delivery: Selecting Manufacture and Development Processes," *Immunomethods,* 4(3):201-9 (1994); and Gregoriadis, "Engineering Liposomes for Drug Delivery: Progress and Problems," *Trends Biotechnol.,* 13(12):527-37 (1995). Mizguchi et al.,

*Cancer Lett.,* 100:63-69 (1996), describes the use of fusogenic liposomes to deliver a protein to cells both in vivo and in vitro.

Dosage, toxicity and therapeutic efficacy of the anti-Cx26 antibodies of the present technology can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In some embodiments, the anti-Cx26 antibodies of the present technology exhibit high therapeutic indices. While anti-Cx26 antibodies of the present technology that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies within a range of circulating concentrations that include the ED50 with little or no toxicity. The dosage may vary within this range depending upon the dosage form employed and the route of administration utilized. For any anti-Cx26 antibodies of the present technology used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the anti-Cx26 antibodies of the present technology, sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example, dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.001-10,000 micrograms per kg body weight. In one embodiment, anti-Cx26 antibodies of the present technology concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, and until the subject shows partial or complete amelioration of symptoms of disease. Thereafter, the patient can be administered a prophylactic regime.

In some embodiments, a therapeutically effective amount of an anti-Cx26 antibodies of the present technology may be defined as a concentration of peptide at the target tissue of $10^{-12}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue. In some embodiments, the doses are administered by single daily or weekly administration, but may also include continuous administration (e.g., parenteral infusion or transdermal application). In some embodiments, the dosage of the anti-Cx26 antibodies of the present technology is provided at a "low," "mid," or "high" dose level. In one embodiment, the low dose is provided from about 0.0001 to about 0.5 mg/kg/h, suitably from about 0.001 to about 0.1 mg/kg/h. In one embodiment, the mid-dose is provided from about 0.01 to about 1.0 mg/kg/h, suitably from about 0.01 to about 0.5 mg/kg/h. In one embodiment, the high dose is provided from about 0.5 to about 10 mg/kg/h, suitably from about 0.5 to about 2 mg/kg/h.

For example, a therapeutically effective amount may partially or completely alleviate one or more symptoms of Clouston Syndrome, including dystrophy of the nails, hypoplasticity and deformation of nails, or increased susceptibility to paronychial infections. For example, a therapeutically effective amount may partially or completely alleviate one or more symptom of Charcot-Marie-Tooth neuropathy, including loss of muscle tissue, loss of touch sensation, atrophy of muscles in the feet, legs, and hands, and hearing impairment. For example, a therapeutically effective amount may partially or completely alleviate one or more symptoms of Keratitis-Ichthyosis-Deafness (KID), including palmoplantar keratoderma, erythrokeratoderma, dry and scaly skin, and hearing loss.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance present methods can be any mammal, including, for example, farm animals, such as sheep, pigs, cows, and horses; pet animals, such as dogs and cats; laboratory animals, such as rats, mice and rabbits. In some embodiments, the mammal is a human.

Use of the Anti-Cx26 Antibodies of the Present Technology

General. The anti-Cx26 antibodies of the present technology are useful in methods known in the art relating to the localization and/or quantitation of Cx30, Cx32, Cx26 protein or a mutant thereof (e.g., for use in measuring levels of the Cx26, Cx30, or Cx32 protein within appropriate physiological samples, for use in diagnostic methods, for use in imaging the polypeptide, and the like). The anti-Cx26 antibodies of the present technology are useful to isolate a Cx26, Cx30, or Cx32 protein by standard techniques, such as affinity chromatography or immunoprecipitation. The anti-Cx26 antibodies of the present technology can facilitate the purification of natural immunoreactive Cx26, Cx30, or Cx32 proteins from biological samples, e.g., mammalian sera or cells as well as recombinantly-produced immunoreactive Cx26, Cx30, or Cx32 proteins expressed in a host system. Moreover, anti-Cx26 antibodies of the present technology can be used to detect an immunoreactive Cx26, Cx30, or Cx32 protein (e.g., in plasma, a cellular lysate or cell supernatant) in order to evaluate the abundance and pattern of expression of the immunoreactive polypeptide. The anti-Cx26 antibodies of the present technology can be used diagnostically to monitor immunoreactive Cx26, Cx30, or Cx32 protein levels in tissue as part of a clinical testing procedure, e.g., to determine the efficacy of a given treatment regimen. As noted above, the detection can be facilitated by coupling (i.e., physically linking) the anti-Cx26 antibodies of the present technology to a detectable substance.

Detection of Cx26, Cx30, or Cx32 protein. An exemplary method for detecting the presence or absence of an immunoreactive Cx26, Cx30, or Cx32 protein in a biological sample involves obtaining a biological sample from a test subject and contacting the biological sample with the anti-Cx26 antibodies of the present technology capable of detecting an immunoreactive Cx26, Cx30, or Cx32 protein such that the presence of an immunoreactive Cx26, Cx30, or Cx32 protein is detected in the biological sample. Detection may be accomplished by means of a detectable label attached to the antibody.

The term "labeled" with regard to the anti-Cx26 antibodies of the present technology antibody is intended to encompass direct labeling of the antibody by coupling (i.e., physically linking) a detectable substance to the antibody, as well as indirect labeling of the antibody by reactivity with another compound that is directly labeled, such as a secondary antibody. Examples of indirect labeling include detection of a primary antibody using a fluorescently-labeled secondary antibody and end-labeling of a DNA probe with biotin such that it can be detected with fluorescently-labeled streptavidin.

In some embodiments, the anti-Cx26 antibodies of the present technology disclosed herein are conjugated to one or more detectable labels. For such uses, the anti-Cx26 antibodies of the present technology antibodies may be detectably labeled by covalent or non-covalent attachment of a chromogenic, enzymatic, radioisotopic, isotopic, fluorescent, toxic, chemiluminescent, nuclear magnetic resonance contrast agent or other label.

Examples of suitable chromogenic labels include diaminobenzidine and 4-hydroxyazo-benzene-2-carboxylic acid. Examples of suitable enzyme labels include malate dehydrogenase, staphylococcal nuclease, $\Delta$-5-steroid isomerase, yeast-alcohol dehydrogenase, $\alpha$-glycerol phosphate dehydrogenase, triose phosphate isomerase, peroxidase, alkaline phosphatase, asparaginase, glucose oxidase, $\beta$-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$p, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is an exemplary isotope where in vivo imaging is used since its avoids the problem of dehalogenation of the $^{125}$I or $^{131}$I-labeled Cx30-, Cx32-, or Cx26-protein binding antibodies by the liver. In addition, this isotope has a more favorable gamma emission energy for imaging (Perkins et al, *Eur. J. Nucl. Med.* 70:296-301 (1985); Carasquillo et al., *J. Nucl. Med.* 25:281-287 (1987)). For example, 111 In coupled to monoclonal antibodies with 1-(P-isothiocyana-tobenzyl)-DPTA exhibits little uptake in non-tumorous tissues, particularly the liver, and enhances specificity of tumor localization (Esteban et al., *J. Nucl. Med.* 28:861-870 (1987)). Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label. Examples of suitable toxin labels include diphtheria toxin, ricin, and cholera toxin.

Examples of chemiluminescent labels include a luminol label, an isoluminol label, an aromatic acridinium ester label, an imidazole label, an acridinium salt label, an oxalate ester label, a luciferin label, a luciferase label, and an aequorin label. Examples of nuclear magnetic resonance contrasting agents include heavy metal nuclei such as Gd, Mn, and iron.

The detection method of the present technology can be used to detect an immunoreactive Cx26, Cx30, or Cx32 protein in a biological sample in vitro as well as in vivo. In vitro techniques for detection of an immunoreactive Cx26, Cx30, or Cx32 protein include enzyme linked immunosorbent assays (ELISAs), Western blots, immunoprecipitations, radioimmunoassay, and immunofluorescence. Furthermore, in vivo techniques for detection of an immunoreactive Cx26, Cx30, or Cx32 protein include introducing into a subject a labeled the anti-Cx26 antibodies of the present technology antibody. For example, the anti-Cx26 antibodies of the present technology antibody can be labeled with a radioactive marker whose presence and location in a subject can be detected by standard imaging techniques. In one embodiment, the biological sample contains Cx26, Cx30, or Cx32 protein molecules from the test subject.

Immunoassay and Imaging. The anti-Cx26 antibodies of the present technology can be used to assay immunoreactive Cx26, Cx30, or Cx32 protein levels in a biological sample (e.g., human plasma) using antibody-based techniques. For example, protein expression in tissues can be studied with classical immunohistological methods. Jalkanen, M. et al., *J. Cell. Biol.* 101:976-985, 1985; Jalkanen, M. et al., *J. Cell. Biol.* 105: 3087-3096, 1987. Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes or other radioactive agent, such as iodine ($^{125}$I, $^{121}$I, $^{131}$I), carbon ($^{14}$C), sulfur ($^{35}$S), tritium ($^3$H), indium ($^{112}$In), and technetium ($^{99}$mTc), and fluorescent labels, such as fluorescein, rhodamine, and green fluorescent protein (GFP), as well as biotin.

In addition to assaying immunoreactive Cx26, Cx30, or Cx32 protein levels in a biological sample, the anti-Cx26 antibodies of the present technology may be used for in vivo imaging of Cx26, Cx30, or Cx32 protein. Antibodies useful for this method include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the anti-Cx26 antibodies of the present technology antibodies by labeling of nutrients for the relevant scFv clone.

An anti-Cx26 antibodies of the present technology which has been labeled with an appropriate detectable imaging moiety, such as a radioisotope (e.g., $^{131}$I, $^{112}$In, $^{99}$mTc), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled the anti-Cx26 antibodies of the present technology antibody will then accumulate at the location of cells which contain the specific target polypeptide. For example, labeled the anti-Cx26 antibodies of the present technology will accumulate within the subject in cells and tissues in which the Cx26, Cx30, or Cx32 protein has localized.

Thus, the present technology provides a diagnostic method of a medical condition, which involves: (a) assaying the expression of immunoreactive Cx26, Cx30, or Cx32 protein by measuring binding of the anti-Cx26 antibodies of the present technology in cells or body fluid of an individual; (b) comparing the amount of immunoreactive Cx26, Cx30, or Cx32 protein present in the sample with a standard reference, wherein an increase or decrease in immunoreactive Cx26, Cx30, or Cx32 protein levels compared to the standard is indicative of a medical condition.

Affinity Purification. The anti-Cx26 antibodies of the present technology may be used to purify immunoreactive Cx26, Cx30, or Cx32 protein from a sample. In some embodiments, the antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10 (1986); Jacoby et al., *Meth. Enzym.* 34 Academic Press, N.Y. (1974)).

The simplest method to bind the antigen to the antibody-support matrix is to collect the beads in a column and pass the antigen solution down the column. The efficiency of this method depends on the contact time between the immobilized antibody and the antigen, which can be extended by using low flow rates. The immobilized antibody captures the antigen as it flows past. Alternatively, an antigen can be contacted with the antibody-support matrix by mixing the antigen solution with the support (e.g., beads) and rotating or rocking the slurry, allowing maximum contact between the antigen and the immobilized antibody. After the binding reaction has been completed, the slurry is passed into a column for collection of the beads. The beads are washed using a suitable washing buffer and then the pure or substantially pure antigen is eluted.

An antibody or polypeptide of interest can be conjugated to a solid support, such as a bead. In addition, a first solid support such as a bead can also be conjugated, if desired, to a second solid support, which can be a second bead or other support, by any suitable means, including those disclosed herein for conjugation of a polypeptide to a support. Accordingly, any of the conjugation methods and means disclosed herein with reference to conjugation of a polypeptide to a solid support can also be applied for conjugation of a first support to a second support, where the first and second solid support can be the same or different.

Appropriate linkers, which can be cross-linking agents, for use for conjugating a polypeptide to a solid support include a variety of agents that can react with a functional group present on a surface of the support, or with the polypeptide, or both. Reagents useful as cross-linking agents include homo-bi-functional and, in particular, hetero-bi-functional reagents. Useful bi-functional cross-linking agents include, but are not limited to, N-SIAB, dimaleimide, DTNB, N-SATA, N-SPDP, SMCC and 6-HYNIC. A cross-linking agent can be selected to provide a selectively cleavable bond between a polypeptide and the solid support. For example, a photolabile cross-linker, such as 3-amino-(2-nitrophenyl) propionic acid can be employed as a means for cleaving a polypeptide from a solid support. (Brown et al., *Mol. Divers*, pp, 4-12 (1995); Rothschild et al., *Nucl. Acids*

*Res.*, 24:351-66 (1996); and U.S. Pat. No. 5,643,722). Other cross-linking reagents are well-known in the art. (See, e.g., Wong (1991), supra; and Hermanson (1996), supra).

An antibody or polypeptide can be immobilized on a solid support, such as a bead, through a covalent amide bond formed between a carboxyl group functionalized bead and the amino terminus of the polypeptide or, conversely, through a covalent amide bond formed between an amino group functionalized bead and the carboxyl terminus of the polypeptide. In addition, a bi-functional trityl linker can be attached to the support, e.g., to the 4-nitrophenyl active ester on a resin, such as a Wang resin, through an amino group or a carboxyl group on the resin via an amino resin. Using a bi-functional trityl approach, the solid support can require treatment with a volatile acid, such as formic acid or trifluoroacetic acid to ensure that the polypeptide is cleaved and can be removed. In such a case, the polypeptide can be deposited as a beadless patch at the bottom of a well of a solid support or on the flat surface of a solid support. After addition of a matrix solution, the polypeptide can be desorbed into a MS.

Hydrophobic trityl linkers can also be exploited as acid-labile linkers by using a volatile acid or an appropriate matrix solution, e.g., a matrix solution containing 3-HPA, to cleave an amino linked trityl group from the polypeptide. Acid lability can also be changed. For example, trityl, monomethoxytrityl, dimethoxytrityl or trimethoxytrityl can be changed to the appropriate p-substituted, or more acid-labile tritylamine derivatives, of the polypeptide, i.e., trityl ether and tritylamine bonds can be made to the polypeptide. Accordingly, a polypeptide can be removed from a hydrophobic linker, e.g., by disrupting the hydrophobic attraction or by cleaving tritylether or tritylamine bonds under acidic conditions, including, if desired, under typical MS conditions, where a matrix, such as 3-HPA acts as an acid.

Orthogonally cleavable linkers can also be useful for binding a first solid support, e.g., a bead to a second solid support, or for binding a polypeptide of interest to a solid support. Using such linkers, a first solid support, e.g., a bead, can be selectively cleaved from a second solid support, without cleaving the polypeptide from the support; the polypeptide then can be cleaved from the bead at a later time. For example, a disulfide linker, which can be cleaved using a reducing agent, such as DTT, can be employed to bind a bead to a second solid support, and an acid cleavable bi-functional trityl group could be used to immobilize a polypeptide to the support. As desired, the linkage of the polypeptide to the solid support can be cleaved first, e.g., leaving the linkage between the first and second support intact. Trityl linkers can provide a covalent or hydrophobic conjugation and, regardless of the nature of the conjugation, the trityl group is readily cleaved in acidic conditions.

For example, a bead can be bound to a second support through a linking group which can be selected to have a length and a chemical nature such that high density binding of the beads to the solid support, or high density binding of the polypeptides to the beads, is promoted. Such a linking group can have, e.g., "tree-like" structure, thereby providing a multiplicity of functional groups per attachment site on a solid support. Examples of such linking group; include polylysine, polyglutamic acid, penta-erythrole and tris-hy-droxy-aminomethane.

Noncovalent Binding Association. An antibody or polypeptide can be conjugated to a solid support, or a first solid support can also be conjugated to a second solid support, through a noncovalent interaction. For example, a magnetic bead made of a ferromagnetic material, which is capable of being magnetized, can be attracted to a magnetic solid support, and can be released from the support by removal of the magnetic field. Alternatively, the solid support can be provided with an ionic or hydrophobic moiety, which can allow the interaction of an ionic or hydrophobic moiety, respectively, with a polypeptide, e.g., a polypeptide containing an attached trityl group or with a second solid support having hydrophobic character.

A solid support can also be provided with a member of a specific binding pair and, therefore, can be conjugated to a polypeptide or a second solid support containing a complementary binding moiety. For example, a bead coated with avidin or with streptavidin can be bound to a polypeptide having a biotin moiety incorporated therein, or to a second solid support coated with biotin or derivative of biotin, such as iminobiotin.

It should be recognized that any of the binding members disclosed herein or otherwise known in the art can be reversed. Thus, biotin, e.g., can be incorporated into either a polypeptide or a solid support and, conversely, avidin or other biotin binding moiety would be incorporated into the support or the polypeptide, respectively. Other specific binding pairs contemplated for use herein include, but are not limited to, hormones and their receptors, enzyme, and their substrates, a nucleotide sequence and its complementary sequence, an antibody and the antigen to which it interacts specifically, and other such pairs knows to those skilled in the art.

A. Diagnostic Uses of the Anti-Cx26 Antibodies of the Present Technology

General. The anti-Cx26 antibodies of the present technology are useful in diagnostic methods. As such, the present technology provides methods using the antibodies in the diagnosis of Cx26, Cx30, or Cx32 protein activity in a subject. The anti-Cx26 antibodies of the present technology may be selected such that they have any level of epitope binding specificity and very high binding affinity to a Cx26, Cx30, or Cx32 protein. In general, the higher the binding affinity of an antibody the more stringent wash conditions can be performed in an immunoassay to remove nonspecifically bound material without removing target polypeptide. Accordingly, the anti-Cx26 antibodies of the present technology useful in diagnostic assays usually have binding affinities of about $10^8$ $M^{-1}$, $10^9$ $M^{-1}$, $10^{10}$ $M^{-1}$, $10^{11}$ $M^{-1}$ or $10^{12}$ $M^{-1}$. Further, it is desirable that the anti-Cx26 antibodies of the present technology antibodies used as diagnostic reagents have a sufficient kinetic on-rate to reach equilibrium under standard conditions in at least 12 h, at least five (5) h, or at least one (1) hour.

The anti-Cx26 antibodies of the present technology antibodies can be used to detect an immunoreactive Cx26, Cx30, or Cx32 protein in a variety of standard assay formats. Such formats include immunoprecipitation, Western blotting, ELISA, radioimmunoassay, and immunometric assays. See Harlow & Lane, Antibodies, A Laboratory Manual (Cold Spring Harbor Publications, New York, 1988); U.S. Pat. Nos. 3,791,932; 3,839,153; 3,850,752; 3,879,262; 4,034,074, 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Biological samples can be obtained from any tissue or body fluid of a subject. In certain embodiments, the subject is at an early stage of cancer. In one embodiment, the early stage of cancer is determined by the level or expression pattern of Cx26, Cx30, or Cx32 protein in a sample obtained from the subject. In certain embodiments, the sample is selected from the group consisting of urine, blood, serum, plasma, saliva, amniotic fluid, cerebrospinal fluid (CSF), and biopsied body tissue.

Immunometric or sandwich assays are one format for the diagnostic methods of the present technology. See U.S. Pat. Nos. 4,376,110, 4,486,530, 5,914,241, and 5,965,375. Such assays use one antibody, e.g., the anti-Cx26 antibodies of the present technology antibody or a population of the anti-Cx26 antibodies of the present technology antibodies immobilized to a solid phase, and another the anti-Cx26 antibodies of the present technology antibody or a population of the anti-Cx26 antibodies of the present technology antibodies in solution. Typically, the solution the anti-Cx26 antibodies of the present technology antibody or population of the anti-Cx26 antibodies of the present technology antibodies is labeled. If an antibody population is used, the population can contain antibodies binding to different epitope specificities within the target polypeptide. Accordingly, the same population can be used for both solid phase and solution antibody. If the anti-Cx26 antibodies of the present technology are used, first and second Cx26, Cx30, or Cx32 protein monoclonal antibodies having different binding specificities are used for the solid and solution phase. Solid phase (also referred to as "capture") and solution (also referred to as "detection") antibodies can be contacted with target antigen in either order or simultaneously. If the solid phase antibody is contacted first, the assay is referred to as being a forward assay. Conversely, if the solution antibody is contacted first, the assay is referred to as being a reverse assay. If the target is contacted with both antibodies simultaneously, the assay is referred to as a simultaneous assay. After contacting the Cx26, Cx30, or Cx32 protein with the anti-Cx26 antibodies of the present technology antibody, a sample is incubated for a period that usually varies from about 10 min to about 24 hr and is usually about 1 hr. A wash step is then performed to remove components of the sample not specifically bound to the anti-Cx26 antibodies of the present technology antibody being used as a diagnostic reagent. When solid phase and solution antibodies are bound in separate steps, a wash can be performed after either or both binding steps. After washing, binding is quantified, typically by detecting a label linked to the solid phase through binding of labeled solution antibody. Usually for a given pair of antibodies or populations of antibodies and given reaction conditions, a calibration curve is prepared from samples containing known concentrations of target antigen. Concentrations of the immunoreactive Cx26, Cx30, or Cx32 protein in samples being tested are then read by interpolation from the calibration curve (i.e., standard curve). Analyte can be measured either from the amount of labeled solution antibody bound at equilibrium or by kinetic measurements of bound labeled solution antibody at a series of time points before equilibrium is reached. The slope of such a curve is a measure of the concentration of the Cx26, Cx30, or Cx32 protein in a sample.

Suitable supports for use in the above methods include, e.g., nitrocellulose membranes, nylon membranes, and derivatized nylon membranes, and also particles, such as agarose, a dextran-based gel, dipsticks, particulates, micro-spheres, magnetic particles, test tubes, microtiter wells, SEPHADEX™ (Amersham Pharmacia Biotech, Piscataway N.J.), and the like. Immobilization can be by absorption or by covalent attachment. Optionally, the anti-Cx26 antibodies of the present technology antibodies can be joined to a linker molecule, such as biotin for attachment to a surface bound linker, such as avidin.

In some embodiments, the present disclosure provides the anti-Cx26 antibodies of the present technology conjugated to a diagnostic agent. The diagnostic agent may comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope. A diagnostic agent is a molecule which is administered conjugated to an antibody moiety, i.e., antibody or antibody fragment, or subfragment, and is useful in diagnosing or detecting a disease by locating the cells containing the antigen.

Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. In some embodiments, the diagnostic agents are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethyl-enediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates may be coupled to the antibodies of the present technology using standard chemistries. The chelate is normally linked to the antibody by a group which enables formation of a bond to the molecule with minimal loss of immunoreactivity and minimal aggregation and/or internal cross-linking. Other methods and reagents for conjugating chelates to antibodies are disclosed in U.S. Pat. No. 4,824,659. Particularly useful metal-chelate combinations include 2-benzyl-DTPA and its monomethyl and cyclohexyl analogs, used with diagnostic isotopes for radio-imaging. The same chelates, when complexed with non-radioactive metals, such as manganese, iron and gadolinium are useful for MRI, when used along with the Cx26, Cx30, or Cx32 protein antibodies of the present technology.

B. Therapeutic Use of the Anti-Cx26 Antibodies of the Present Technology

General. In some aspects, the anti-Cx26 antibodies of the present technology are useful in methods disclosed herein provide therapies for the prevention, amelioration or treatment of genetic disorders associated with a mutation in the connexin 30 (Cx30), connexin 32 (Cx32) and/or connexin 26 (Cx26) hemichannel. Genetic disorders associated with a mutation in the connexin 30 (Cx30), connexin 32 (Cx32) and/or connexin 26 (Cx26) hemichannel include ectodermal dysplasia 2, Clouston type (OMIM No. 129500), Keratitis-ichthyosis-deafness syndrome (KIDS; OMIM No. 148210), and/or type X Charcot-Marie-Tooth neuropathy (CMTX1; OMIM No. 302800).

In some embodiments, the condition associated with mutant Cx26, Cx32, and/or Cx30 hemichannels. In some embodiments, the genetic disorder is associated with a mutation in the connexin 30 (Cx30), connexin 32 (Cx32), connexin 26 (Cx26) hemichannel or a combination thereof. In some embodiments, the genetic disorder is ectodermal dysplasia 2, Clouston type (OMIM No. 129500). In some embodiments, the genetic disorder is Keratitis-ichthyosis-deafness syndrome (KIDS; OMIM No. 148210). In some embodiments, the genetic disorder is type X Charcot-Marie-Tooth neuropathy (CMTX1; OMIM No. 302800).

In one aspect, the present technology relates to alleviating one or more symptoms of Clouston Syndrome in a subject in need thereof, the method comprising: administering a therapeutically effective amount of an antibody or antigen binding fragment thereof comprising a heavy chain immunoglobulin variable domain ($V_H$) and a light chain immunoglobulin variable domain ($V_L$), wherein the $V_H$ comprises complementarity determining regions $V_H$ CDR1, $V_H$ CDR2 and $V_H$ CDR3, wherein the $V_H$ CDR1 comprises an amino acid sequence set forth in SEQ ID NO: 3, $V_H$ CDR2 comprises an amino acid sequence set forth in SEQ ID NO: 4, and $V_H$ CDR3 comprises an amino acid sequence set forth in SEQ ID NO: 5; and wherein the $V_L$ comprises complementarity determining regions $V_L$ CDR1, $V_L$ CDR2 and $V_L$ CDR3, wherein the $V_L$ CDR1 comprises an amino acid sequence set forth in SEQ ID NO: 6, $V_L$ CDR2 comprises an amino acid sequence set forth in SEQ ID NO: 7, and $V_L$ CDR3 comprises an amino acid sequence set forth in SEQ ID NO: 8. In some embodiments, the $V_H$ comprises an amino acid sequence set forth in SEQ ID NO: 11. In some embodiments, the $V_L$ comprises an amino acid sequence set forth in SEQ ID NO: 12. In some embodiments, the $V_H$ is encoded by a nucleic acid sequence set forth in SEQ ID NO: 9. In some embodiments, the $V_L$ is encoded by a nucleic acid sequence set forth in SEQ ID NO: 10. In some embodiments, the antibody or antigen binding fragment thereof specifically binds to the extracellular loops EC1 and/or EC2 of connexin 30 (Cx26), connexin 32 (Cx32), connexin 30 (Cx30) or a mutant thereof. In some embodiments, the EC1 comprises a sequence set forth in SEQ ID NO: 1 (NTLQP). In some embodiments, the EC2 comprises a sequence set forth in SEQ ID NO: 2 (PN). In some embodiments, anti-Cx26 antibodies of the present technology inhibits formation of a gap junction by binding to a hemichannel. In some embodiments, anti-Cx26 antibodies of the present technology prevent cell death or dysfunction by reducing or blocking the transfer of ions and molecules across the cells plasma membrane through mutant connexin hemichannels with augmented activity. In some embodiments, the one or more symptoms is dystrophy of the nails, hypoplasticity and deformation of nails, or increased susceptibility to paronychial infections.

In one aspect, the present technology relates to alleviating one or more symptoms of Charcot-Marie-Tooth neuropathy in a subject in need thereof, the method comprising: administering a therapeutically effective amount of an antibody or antigen binding fragment thereof comprising a heavy chain immunoglobulin variable domain ($V_H$) and a light chain immunoglobulin variable domain ($V_L$), wherein the $V_H$ comprises complementarity determining regions $V_H$ CDR1, VHI CDR2 and $V_H$ CDR3, wherein the $V_H$ CDR1 comprises an amino acid sequence set forth in SEQ ID NO: 3, $V_H$ CDR2 comprises an amino acid sequence set forth in SEQ ID NO: 4, and $V_H$ CDR3 comprises an amino acid sequence set forth in SEQ ID NO: 5; and wherein the $V_L$ comprises complementarity determining regions $V_L$ CDR1, $V_L$ CDR2 and $V_L$ CDR3, wherein the $V_L$ CDR1 comprises an amino acid sequence set forth in SEQ ID NO: 6, $V_L$ CDR2 comprises an amino acid sequence set forth in SEQ ID NO: 7, and $V_L$ CDR3 comprises an amino acid sequence set forth in SEQ ID NO: 8. In some embodiments, the $V_H$ comprises an amino acid sequence set forth in SEQ ID NO: 11. In some embodiments, the $V_L$ comprises an amino acid sequence set forth in SEQ ID NO: 12. In some embodiments, the $V_H$ is encoded by a nucleic acid sequence set forth in SEQ ID NO: 9. In some embodiments, the $V_L$ is encoded by a nucleic acid sequence set forth in SEQ ID NO: 10. In some embodiments, the antibody or antigen binding fragment thereof specifically binds to the extracellular loops EC1 and/or EC2 of connexin 30 (Cx26), connexin 32 (Cx32), connexin 30 (Cx30) or a mutant thereof. In some embodiments, the EC1 comprises a sequence set forth in SEQ ID NO: 1 (NTLQP). In some embodiments, the EC2 comprises a sequence set forth in SEQ ID NO: 2 (PN). In some embodiments, anti-Cx26 antibodies of the present technology inhibits formation of a gap junction by binding to a hemichannel. In some embodiments, anti-Cx26 antibodies of the present technology prevent cell death or dysfunction by reducing or blocking the transfer of ions and molecules across the cells plasma membrane through mutant connexin hemichannels with augmented activity. In some embodiments, the one or more symptoms is loss of muscle tissue, loss of touch sensation, atrophy of muscles in the feet, legs, and hands, or hearing impairment.

In one aspect, the present technology relates to alleviating one or more symptoms of Keratitis-Ichthyosis-Deafness (KID) in a subject in need thereof, the method comprising: administering a therapeutically effective amount of an antibody or antigen binding fragment thereof comprising a heavy chain immunoglobulin variable domain ($V_H$) and a light chain immunoglobulin variable domain ($V_L$), wherein the $V_H$ comprises complementarity determining regions $V_H$ CDR1, $V_H$ CDR2 and $V_H$ CDR3, wherein the $V_H$ CDR1 comprises an amino acid sequence set forth in SEQ ID NO: 3, $V_H$ CDR2 comprises an amino acid sequence set forth in SEQ ID NO: 4, and $V_L$ CDR3 comprises an amino acid sequence set forth in SEQ ID NO: 5; and wherein the $V_L$ comprises complementarity determining regions $V_L$ CDR1, $V_L$ CDR2 and $V_L$ CDR3, wherein the $V_L$ CDR1 comprises an amino acid sequence set forth in SEQ ID NO: 6, $V_L$ CDR2 comprises an amino acid sequence set forth in SEQ ID NO: 7, and $V_L$ CDR3 comprises an amino acid sequence set forth in SEQ ID NO: 8. In some embodiments, the $V_H$ comprises an amino acid sequence set forth in SEQ ID NO: 11. In some embodiments, the $V_L$ comprises an amino acid sequence set forth in SEQ ID NO: 12. In some embodiments, the $V_L$ is encoded by a nucleic acid sequence set forth in SEQ ID NO: 9. In some embodiments, the $V_L$ is encoded by a nucleic acid sequence set forth in SEQ ID NO: 10. In some embodiments, the antibody or antigen binding fragment thereof specifically binds to the extracellular loops EC1 and/or EC2 of connexin 30 (Cx26), connexin 32 (Cx32), connexin 30 (Cx30) or a mutant thereof. In some embodiments, the EC1 comprises a sequence set forth in SEQ ID NO: 1 (NTLQP). In some embodiments, the EC2 comprises a sequence set forth in SEQ ID NO: 2 (PN). In some embodiments, anti-Cx26 antibodies of the present technology inhibits formation of a gap junction by binding to a hemichannel. In some embodiments, anti-Cx26 antibodies of the present technology prevent cell death or dysfunction by reducing or blocking the transfer of ions and molecules across the cells plasma membrane through mutant connexin hemichannels with augmented activity. In some embodiments, the one or more symptoms is palmoplantar keratoderma, erythrokeratoderma, dry and scaly skin, or hearing loss.

In some embodiments, the antibody or antigen binding fragment thereof is an antibody, scFv, (scFv)$_2$, scFv-Fc, Fab, Fab', F(ab')$_2$ or an scFv-Fc antibody. In some embodiments, the antibody or antigen binding fragment thereof is an scFv-Fc antibody. In some embodiments, the scFv-Fc antibody is abEC1.1 or abEC1.1m.

Thus, for example, one or more the anti-Cx26 antibodies of the present technology may be: (1) co-formulated and administered or delivered alone or simultaneously in a combined formulation with other active agents or the anti-Cx26 antibodies of the present technology; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used. Administering such combinations of the anti-Cx26 antibodies of the present technology and other active agents can result in synergistic biological effect when administered in a therapeutically effective amount to a subject suffering from a medical disease or condition and in need of treatment. An advantage of such an approach is that lower doses of the anti-Cx26 antibodies of the present technology and/or other active agents may be needed to prevent, ameliorate or treat a subject suffering from, or predisposed to, ectodermal dysplasia 2, Clouston type (OMIM No. 129500), Keratitis-ichthyosis-deafness syndrome (KIDS; OMIM No. 148210), and/or type X Charcot-Marie-Tooth neuropathy (CMTX1; OMIM No. 302800) in a subject. Further, potential side-effects of treatment may be avoided by use of lower dosages of the anti-Cx26 antibodies of the present technology and/or other active agents.

The anti-Cx26 antibodies of the present technology are described herein such as abEC1.1, abEC1.1m, etc. are useful to prevent or treat disease. Specifically, the disclosure provides for both prophylactic and therapeutic methods of treating a subject suffering from, or predisposed to, ectodermal dysplasia 2, Clouston type (OMIM No. 129500), Keratitis-ichthyosis-deafness syndrome (KIDS; OMIM No. 148210), and/or type X Charcot-Marie-Tooth neuropathy (CMTX1; OMIM No. 302800). Accordingly, the present methods provide for the prevention and/or treatment a subject suffering from, or predisposed to, ectodermal dysplasia 2, Clouston type (OMIM No. 129500), Keratitis-ichthyosis-deafness syndrome (KIDS; OMIM No. 148210), and/or type X Charcot-Marie-Tooth neuropathy (CMTX1; OMIM No. 302800) in a subject by administering an effective amount of the anti-Cx26 antibodies of the present technology to a subject in need thereof to restore of the function of the mutant connexin hemichannel. The present technology relates to the treatment of a subject suffering from, or predisposed to, ectodermal dysplasia 2, Clouston type (OMIM No. 129500), Keratitis-ichthyosis-deafness syndrome (KIDS; OMIM No. 148210), and/or type X Charcot-Marie-Tooth neuropathy (CMTX1; OMIM No. 302800) in mammals through administration of therapeutically effective amounts of the anti-Cx26 antibodies of the present technology as disclosed herein, such as abEC1.1, abEC1.1m, etc. to subjects in need thereof.

Determination of the Biological Effect of the Anti-Cx26 Antibodies of the Present Technology.

In various embodiments, suitable in vitro or in vivo assays are performed to determine the effect of a specific therapeutic based on the anti-Cx26 antibodies of the present technology and whether its administration is indicated for treatment. In various embodiments, in vitro assays can be performed with representative cell lines, such as HeLa DH cells. In various embodiments, in vitro assays can be performed with representative animal models, such as mice harboring $Cx30^{488V}$ or $Cx30^{G12R}$; $Cx26^{G45E}$, or $Cx26^{D50N}$, or $Cx26^{S17F}$ mutations. Other mice harboring mutations such as $Cx32^{D178Y}$ or $Cx32^{S85C}$ or $Cx32^{F235C}$ has also been contemplated. These experiments may be used to determine if a given anti-Cx26 antibodies of the present technology exerts the desired effect in inhibiting the activity of mutant Cx26, Cx32, and/or Cx30 hemichannels, or restoration of the function of the mutant connexin hemichannel. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

In some embodiments, connexin hemichannels activity is determined by assays well known in the art, including, but not limited to patch clamp. In some embodiments, connexin hemichannels activity is determined by assays that measure biological activity in animal models harboring mutations that augment connexin hemichannel activity, such as $Cx30^{488V}$ or $Cx30^{G12R}$; $Cx26^{G45E}$, or $Cx26^{D50N}$, or $Cx26^{S17F}$ mutations. Other mice harboring mutations such as $Cx32^{D178Y}$, or $Cx32^{S85C}$, or $Cx32^{F235C}$ has also been contemplated. In some embodiments, connexin hemichannels activity is determined by assays that measure the rescue of mutant phenotype of the animal models.

Modes of Administration and Effective Dosages

Any method known to those in the art for contacting a cell, organ or tissue with a peptide may be employed. Suitable methods include in vitro, ex vivo, or in vivo methods. In vivo methods typically include the administration of an immunoglobulin-related composition, such as those described above, to a mammal, suitably a human. When used in vivo for therapy, the anti-Cx26 antibodies of the present technology are administered to the subject in effective amounts (i.e., amounts that have desired therapeutic effect). The dose and dosage regimen will depend upon the degree of the symptoms in the subject, the characteristics of the particular immunoglobulin used, e.g., its therapeutic index, the subject, and the subject's history.

The effective amount may be determined during pre-clinical trials and clinical trials by methods familiar to physicians and clinicians. An effective amount of an immunoglobulin useful in the methods may be administered to a mammal in need thereof by any of a number of well-known methods for administering pharmaceutical compounds. The immunoglobulin may be administered systemically or locally.

C. Kits

The present technology provides kits for the detection and/or treatment of mutant Cx26-, Cx30-, or Cx32-associated disease, comprising at least one immunoglobulin-related composition of the present technology (e.g., any antibody or antigen binding fragment described herein), or a functional variant (e.g., substitutional variant) thereof. Optionally, the above described components of the kits of the present technology are packed in suitable containers and labeled for diagnosis and/or treatment of mutant Cx26-, Cx30-, or Cx32-associated disease. The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic or diagnostic products, that contain information about, for example, the indications, usage, dosage, manufacture, administration, contraindications and/or warnings concerning the use of such therapeutic or diagnostic products.

The kits are useful for detecting the presence of an immunoreactive Cx26, Cx30, or Cx32 protein in a biological sample, e.g., any body fluid including, but not limited to, e.g., serum, plasma, lymph, cystic fluid, urine, stool, cerebrospinal fluid, ascitic fluid or blood and including biopsy samples of body tissue. For example, the kit can comprise: one or more humanized, chimeric, or bispecific anti-Cx26 antibodies of the present technology (or antigen binding fragments thereof) capable of binding a Cx26, Cx30, or Cx32 protein in a biological sample; means for determining the amount of the Cx26, Cx30, or Cx32 protein in the sample; and means for comparing the amount of the immunoreactive Cx26, Cx30, or Cx32 protein in the sample with a standard. One or more of the anti-Cx26 antibodies may be labeled. The kit components, (e.g., reagents) can be packaged in a suitable container. The kit can further comprise instructions for using the kit to detect the immunoreactive Cx26, Cx30, or Cx32 protein.

For antibody-based kits, the kit can comprise, e.g., 1) a first antibody, e.g. a humanized, or chimeric Cx26, Cx30, or Cx32 antibody of the present technology (or an antigen binding fragment thereof), attached to a solid support, which binds to a Cx26, Cx30, or Cx32 protein; and, optionally; 2) a second, different antibody which binds to either the Cx26, Cx30, or Cx32 protein or to the first antibody, and is conjugated to a detectable label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit, e.g., for detection of a Cx26, Cx30, or Cx32 protein in vitro or in vivo, or for treatment of mutant Cx26, Cx30, or Cx32-associated disease in a subject in need thereof. In certain embodiments, the use of the reagents can be according to the methods of the present technology.

EXAMPLES

The present technology is further illustrated by the following examples, which should not be construed as limiting in any way. For each of the examples below, any immunologic binding agent, such as IgG, IgM, IgA, IgD, IgE, and genetically modified IgG, and fragments thereof described herein could be used. By way of example, but not by limitation, the scFv-Fc antibodies used in the examples below could be abEC1.1, abEC1.1m, etc.

Example 1: Selection of Antibodies from Phage Display Libraries

A peptide corresponding to residues 41-56 of Cx26 (KEVWGDEQADFVCNTL=pepEC1.1 (SEQ ID NO: 53)) was synthesized and labeled with biotin at the N-terminus (Chinese Peptide Company, Hangzhou Economic and Technological Development Zone, China).

Streptavidin-coated magnetic beads (Pierce, Cat. No. 88817) were mixed in Tween phosphate buffer (PBST) with biotinylated pepEC1.1 and screened against a scFv combinatorial library expressed in phage. Zhang et al., *Proc. Natl. Acad. Sci. U.S.A.* 109: 15728-15733 (2012).

For the phage panning process specific clones were enriched by binding to immobilized pepEC1.1, followed by elution with Glycine-HCl (pH 2.2) and repropagation of phage in XL1-Blue cells. Barbas et al., Phage Display: A Laboratory Manual. (Cold Spring Harbor Publications, New York, 2004); Lee et al., Nat. Protoc. 2:3001-3008 (2007). After four rounds of panning, 150 colonies were picked and analyzed by phage ELISA (see below).

Positive colonies were sequenced and analyzed using the international ImMunoGeneTics information system®. Lefranc et al., *Nucleic Acids Res.* 43: D413-D422 (2015). The scFv-Fc human monoclonal antibodies were selected by panning a phage-display library using a bait peptide derived from the EC1 domain of Cx26 and used in these assays.

Complementarity determining regions 3 (CDR3s) were aligned with Clustal X. Larkin et al., *Bioinformatics* 23:2947-2948 (2007). A phylogenetic tree was constructed using CLC Genomics Workbench 8.0 (CLCbio).

The genes encoding the scFv candidates, identified by analysis of the phylogenetic tree, were cloned into a modified pFUSE expression vector (Invivogen, Cat. No. pfuse-hg1fc2) to obtain scFv-Fc fusion proteins comprising the entire Fc domain of human immunoglobulin G1 (IgG1).

293-F cells were transfected with the scFv-Fc vectors and the expressed fusion proteins were purified using HiTrap Protein A HP columns (GE Healthcare, Cat. No. 17-0403-03) with ÄKTA purifier 100 (GE Healthcare). After purification, the buffer was exchanged to PBS (pH 7.4). The purified scFv-Fc proteins were kept either at 4° C., for short-term storage, or at −80° C. for longer-term conservation.

96-well ELISA plates (Corning Costar, Cat. No. 3690) were filled with 25 µl per well of a solution containing avidin (1 µg/well; Pierce, Cat. No. 21121) dissolved in CBS buffer (pH 9.0). Plates were incubated at 4° C. overnight or 37° C. for 1 hr. After washing with PBS-T buffer (0.05% TWEEN20 in PBS), 25 µl of a pepEC1.1 solution (0.05 µg/well, diluted in PBS) was add to each well and incubated for 1 hr at 37° C. Wells were washed twice and blocked with 150 μl per well of M-PBST (5% milk in PBST) and incubated for 1 hr at 37° C. After discarding the blocking solution, 25 μl of abEC1.1 solution (1 mg/ml, diluted in M-PBST buffer, dilution factor 1:100) were added and incubated for 1 hr at 37° C., then washed 8 times. Each well then received 50 μl of a solution containing goat anti-Human horseradish peroxidase-conjugated antibody (Sigma, Cat. No. A0170, 1 ml) diluted in M-PBST buffer (dilution factor 1:5000). Plates were incubated for 1 hr at 37° C. and then washed 8 times. Finally, 50 μl of substrate ABTS solution (Roche, Cat. No. 11684302001) was added to each well and incubated for 20 min at room temperature. Optical density (OD) was read out at 405 nm on a PerkinElmer Enspire plate reader.

Relative affinity and specificity of scFv-phages and soluble scFvs was assessed against the pepEC1.1 antigen. To this end, 10 μg/ml of pepEC1.1 were used to coat a microtiter plate at 4° C. overnight. Any remaining binding sites were blocked with Blotto (5% w/v of Bovine Serum Albumin in PBST; bovine serum albumin was purchased from Thermo Fisher, Cat. No. 23210). Approximately 25 μl per well of scFv-phage or soluble scFv supernatant from overnight cell cultures was added and incubated for 1 hat 37cc. For scFv-phage ELISA (Tong et al., *American journal of physiology. Cell physiology* 300: C1055-1064 (2011)), after washing, 25 μl of anti-MB mAb horseradish peroxidase (HRP) conjugate (Amersham Pharmacia) diluted 1:1000 in Blotto was added for 30 min at 37° C. For ELISA using soluble scFv, anti-Human horseradish peroxidase conjugate (Sigma, Cat. No. A0170-1 ml) in Blotto was added and incubated for 30 min at 37° C. Detection was accomplished by adding 50 μl of ABTS solution (Roche, Cat. No. 11684302001) and absorbance was measured at 405 nm. The binding affinity of the scFv-Fc recombinant antibodies for pepEC1.1 was quantified by ELISA.

Example 2: Use of in Silico Modeling to Identify Binding Amino Acids

The atomic model of the heavy chain ($V_H$) and light chain ($V_L$) without linker, derived from the crystal structure of the scFv antibody domain, was docked to the extracellular domain of a model of a Cx26 homomeric hemichannel, embedded in the plasma membrane, using the ClusPro 2.0 server in the antibody docking mode. Among the 50 docking configuration generated by the software, the only one in which the three CDRs of $V_H$ faced the EC1 loop of Cx26 was selected, and its stability was tested by performing a 100 ns molecular dynamics simulation using the Gromacs 4 package and the CHARMM 36 force field.

Temperature T was kept fixed at 300 K in all simulations, and, where stated, the pressure P was fixed at 1 atm using Berendsen thermostat and barostat. Fast smooth Particle-Mesh Ewald summation was used for long-range electrostatic interactions, with a cut off of 1.0 nm for the direct interactions.

After molecular dynamics thermalization, a stable configuration was obtained in which $V_H$ and $V_L$ interacted with three adjacent protomers of the Cx26 hemichannel. Therefore, a second symmetrically docked pair of $V_H$ and $V_L$ was added and obtained a new configuration in which the pore lumen was completely covered.

The last 10 ns of the computer simulation was analyzed and searched for antibody-connexin residue pairs that interacted stably. Interaction probability was measured as the fraction of the simulation time in which the distance between each pair of residues was less than an arbitrarily pre-assigned threshold (2 Å).

Example 3: Patch-Clamp Assay of Antibody Effect on Hemichannel Electrical Conductance Glass coverslips with adherent connexin-expressing cells were continuously superfused at 2 ml/min at 20-23° C. with an extracellular solution (EXP) containing 140 mM NaCl, 5 mM KCl, 10 mM HEPES, 2 mM sodium pyruvate, 4 mM tetraethylarnrnonium chloride (TEA-CI), 4 mM CsCl, 5 mM glucose, and a reduced (0.2 mM) $Ca^{2+}$ concentration (pH 7.4, 323 mOsm). Cells were selected for patch clamp recordings by visual inspection using an optical microscope coupled to a dual patch clamp system.

Patch pipettes were filled with an intracellular solution containing 115 mM KAsp, 10 mM NaCl, 10 mM KCl, 1 mM $MgCl_2$, 10 mM HEPES, 1 mM $CaCl_2$), and 5 mM BAPTA tetrapotassium salt (pH 7.2, 311 mOsm) and filtered through 0.22-mm pores (Millipore). Filled pipettes had resistances of 4-6 MΩ when immersed in EXP. Hemichannel currents were assayed in EXP under whole cell patch clamp recording conditions.

The antibody to be assayed was dissolved in EXP and delivered through a glass micropipette pulled to a 4 μm diameter tip from B150F glass (World Precision Instruments, Sarasota, USA). During antibody delivery, the superfusion was stopped.

Example 4: Mouse Genotyping of $Cx30^{A88V/A88V}$ Mice

Genotyping protocols were performed by PCR on extracted mouse tail tips as recommended by the provider (European Mouse Mutant Archive). Both male and female mice, aged 6 to 8 weeks, mutant as well as wild type littermates (used for controls) were treated either topically or systemically (see below). Genotyping details are as follows: STRAIN: CX30A88V (EM07626)

```
PRIMER A88V for (SEQ ID NO: 13):
5'-GGT CGA AGG AAC CTT TCA CAGG-3'

PRIMER A88V rev (SEQ ID NO: 14):
5'-GCT ACC ATC ACG TGC TCT TTG G-3'
```

PRIMER A88V for 15 pm/total volume 30 μl Tm: 68° C.
PRIMER A88V rev 15 pm/total volume 30 μl Tm: 68° C.
PCRMIX

| | |
|---|---|
| DNTPS (2 mM) | 3 μl |
| PCR BUFFER 10× | 3 μl |
| PRIMER A88V for | (0.5 pm/μl) |
| PRIMER A88V rev | (0.5 pm/μl) |
| $H_2O$ | |
| TAQ POLYMERASE (5 U/μl) | 0.25 μl |
| DNA | 2 μl |
| TOTAL | 30 μl |

PCR program
1) 95° C. for 2' 00"
2) 95° C. for 1'00"
3) 65° C. for 1'00"
4) 72° C. for 1'00"
5) step 2 to step 4×45 repeats
6) 72° C. X 10'00"
7) 4° C. forever
8) End As shown in FIG. 12, PCR reactions from genomic DNA from wild type mice generated the expected band at 423 bp. Homozygous Cx30$^{A88V/A88V}$ mutants showed only the predicted band at 481 bp, and Cx30$^{+/A88V}$ heterozygous mice showed both bands.

Figure 1:
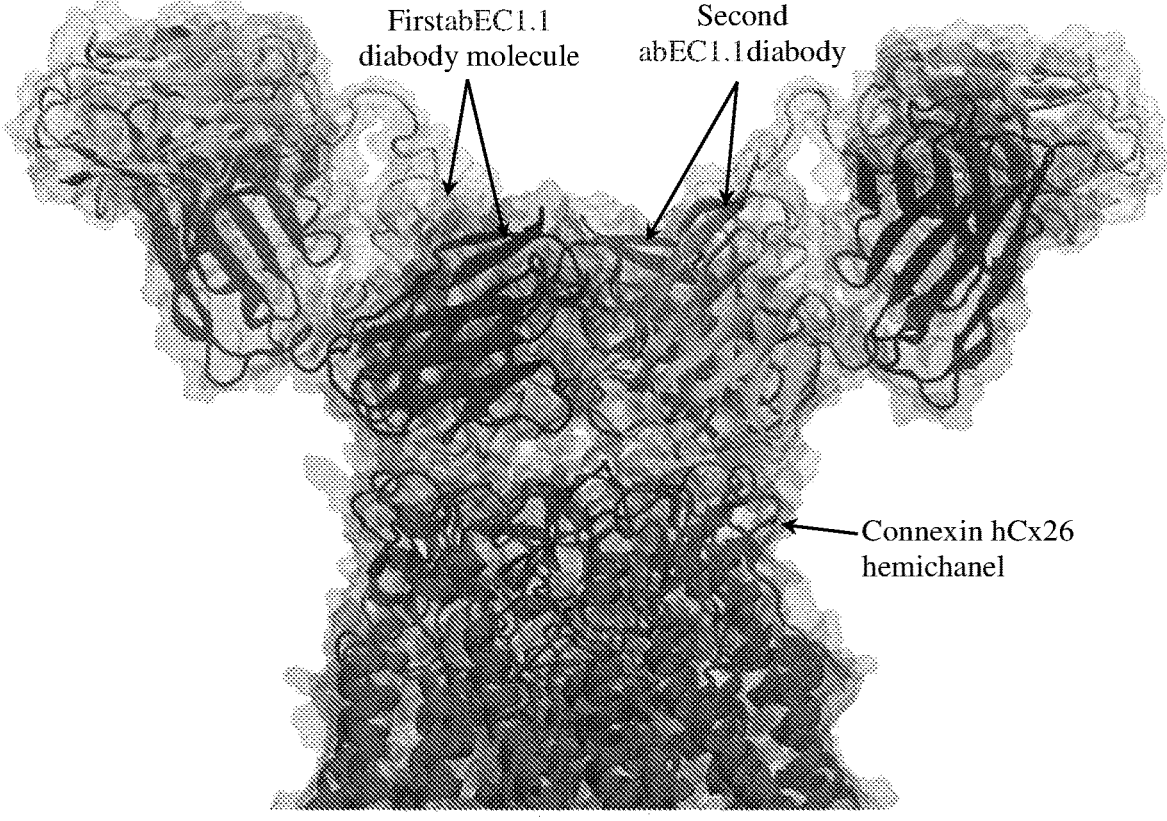
FIG. 1 shows the results of molecular modeling studies demonstrating simultaneous binding of two abEC1.1 diabody-Fc molecules to a human connexin 26 (hCx26) hemichannel molecule. A side view is shown. The scFv domains of the two diabodies, and the connexin hemichannel are indicated. Each antibody is a diabody-Fc (a dimer of two scFv-Fc polypeptides). The scFv domains of the two different diabodies, and the connexin hemichannel are marked. Fc domains of the antibodies are not shown.

Example 5: Two Different abEC1.1 Antibodies Simultaneously Bind the Extracellular Region of a Single Connexin Hemichannel In silico modeling analysis of abEC1.1 interaction with the Cx26 hemichannel was performed. This analysis identified critically important extracellular domain amino acids that are conserved in connexin 30 (Cx30) and connexin 32 (Cx32). As shown in FIG. 1, an antibody pair binds to a Cx26 hemichannel. The modeling studies confirmed the results from binding studies, which suggested a stoichiometry of binding of two diabody molecules to one Cx26 hemichannel molecule (data not shown). These data show that two different abEC1.1 antibody molecules simultaneously bind the extracellular region of a single connexin hemichannel.

Example 6: The Anatomy of Interaction of abEC1.1 and Human Cx26 Hemichannel

Figure 2A:
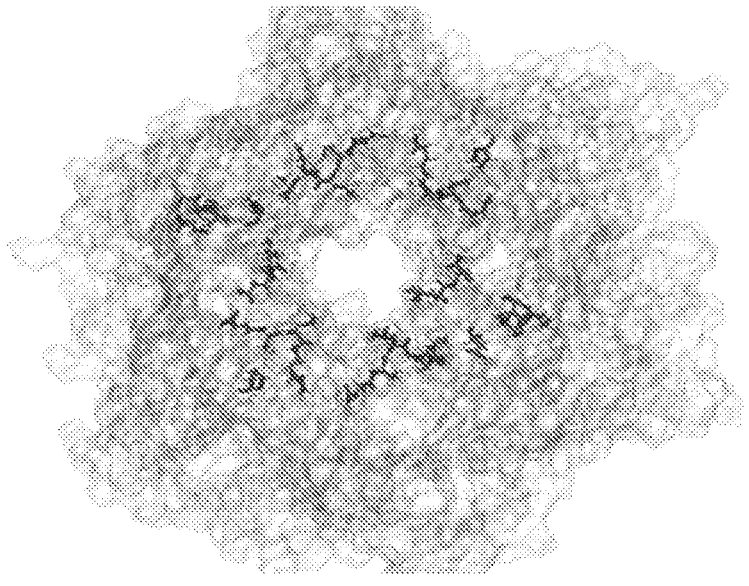
FIG. 2A shows a schematic representation of a Cx26 hemichannel viewed from the extracellular side, displaying the amino acid residues of hemichannel that are predicted to interact with abEC1.1. The hemichannel residues interacting with abEC1.1 (percentage of interaction >55%) are shown in dark color over the faint background of rest of the hemichannel.
Figure 2B:
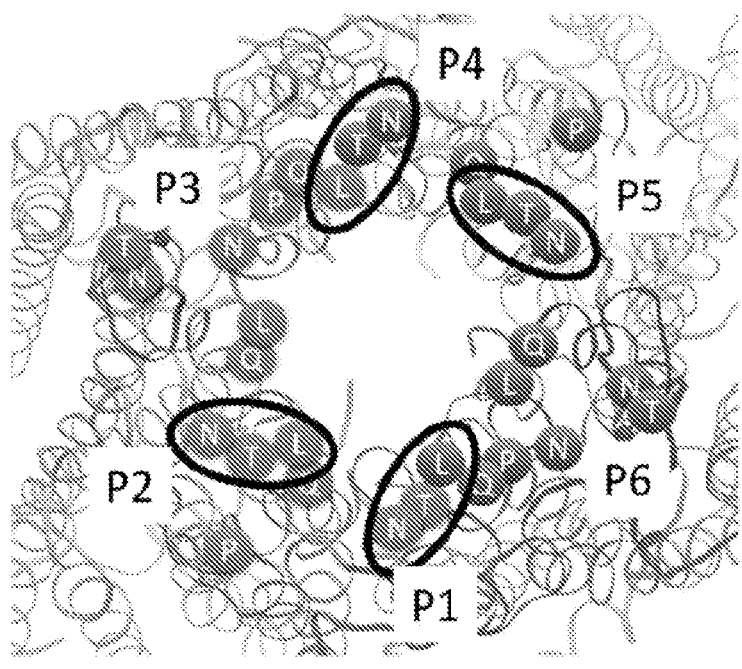
FIG. 2B shows a schematic representation of a Cx26 hemichannel showing different protomers (P1 to P6) of the Cx26 hemichannel. Labeled circles represent the positions of the alpha carbon of the amino acid residues shown in FIG. 2A. Different shades of residues represent the binding regions of the two scFvs present in each diabody. The N-T-L motif is surrounded by an ellipse to indicate that the three residues interact with the diabody.
Figure 2C:
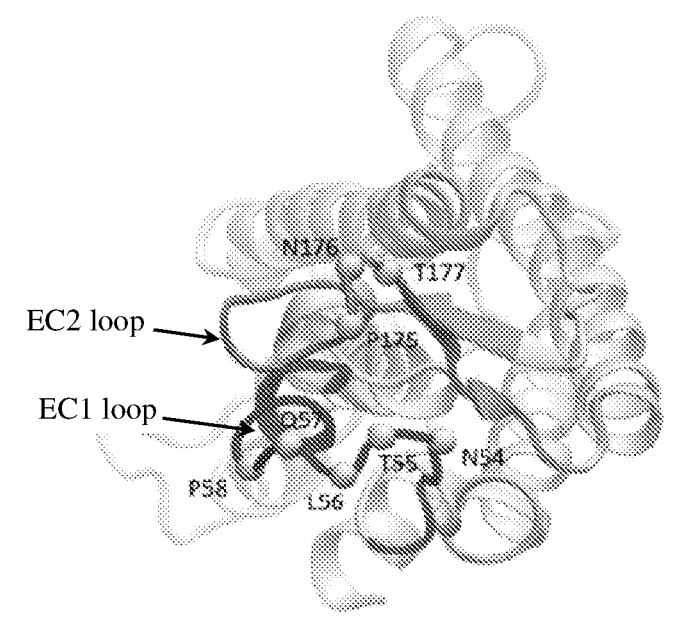
FIG. 2C shows a top view of a single protomer of an Cx26 hemichannel showing the positions of the amino acid residues that are potentially involved in the interaction with the hemichannel. The EC1 and EC2 loops are shown.
Figure 2D:
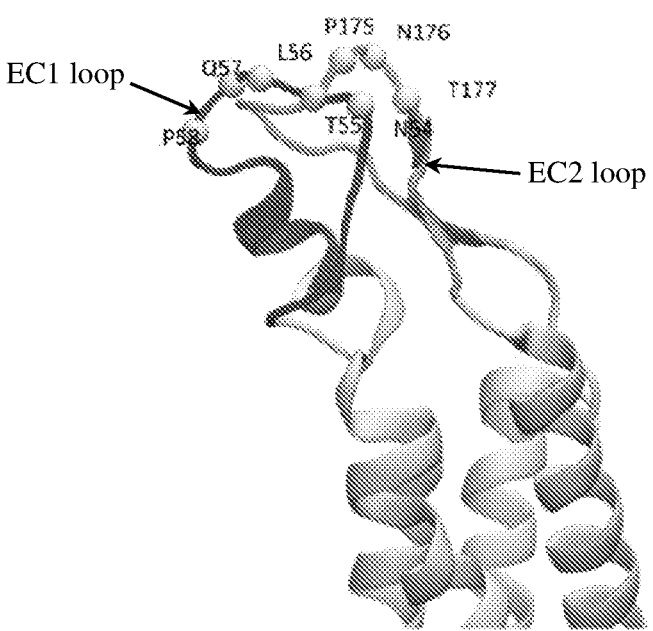
FIG. 2D shows a side view of a single protomer of an Cx26 hemichannel indicating the positions of the amino acid residues potentially involved in the interaction with hemichannel. The EC1 and EC2 loops are marked.
Figure 3A:
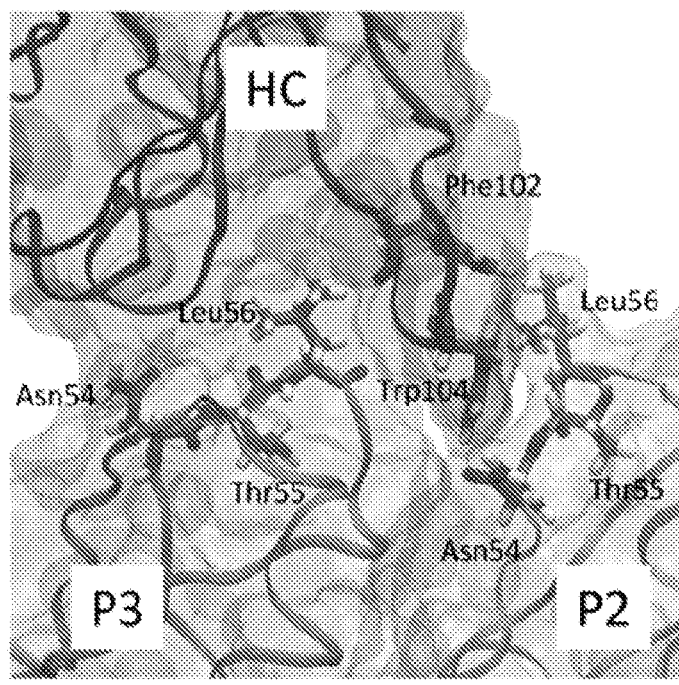
FIGS. 3A-3D show representations of the predicted interaction of abEC1.1 with the Cx26 hemichannel, as predicted by molecular dynamics simulation.
Figure 3B:
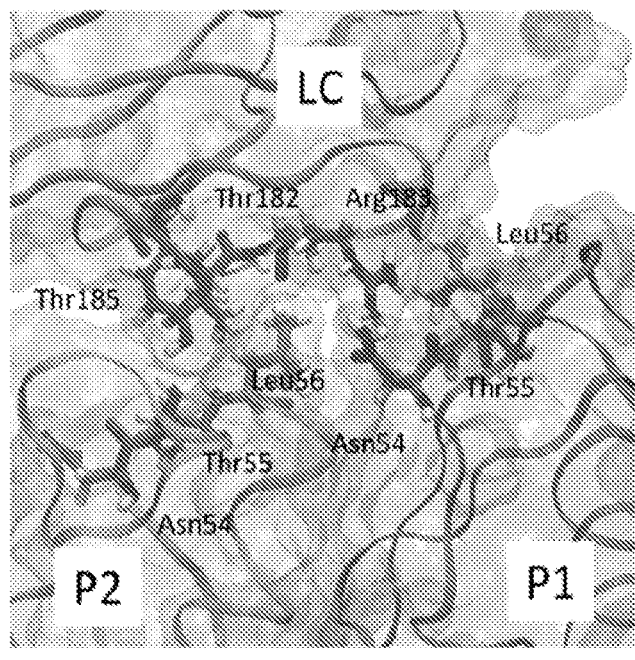
Figure 3C:
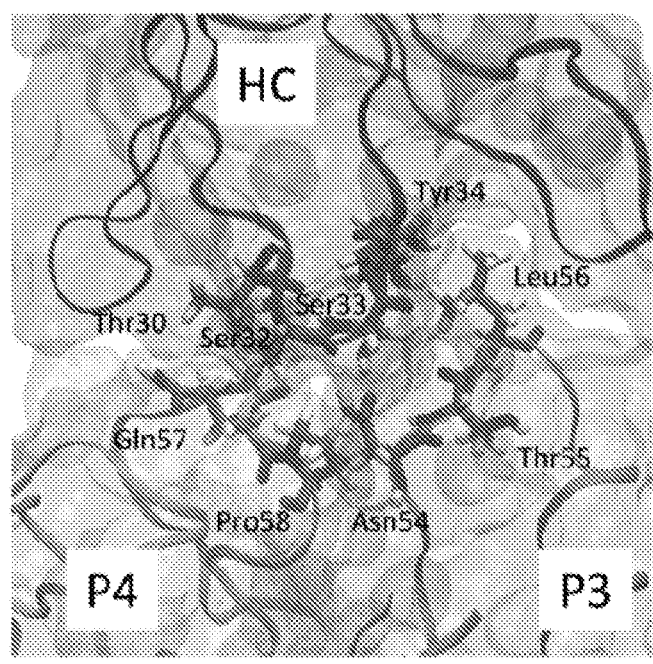
Figure 3D:
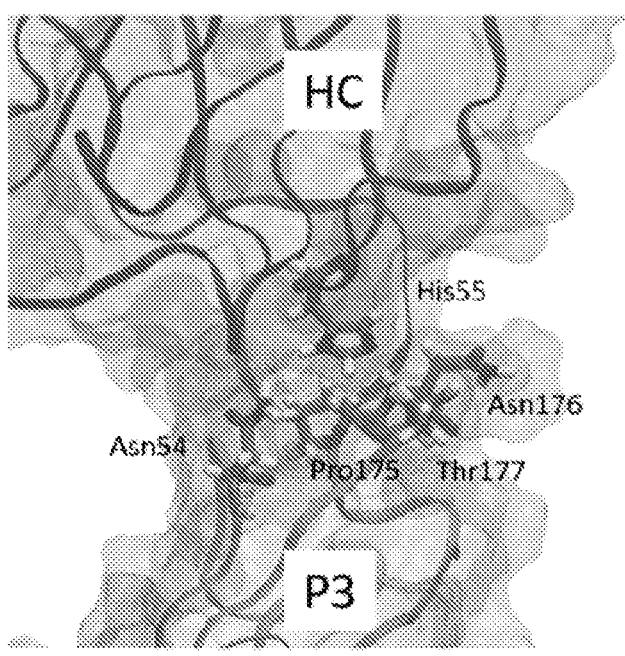

Modeling studies were performed to understand the details of interaction of abEC1.1 antibody with the Cx26 hemichannel. As shown in FIG. 2A, amino acid residues of each of the protomers that interact with the abEC1.1 antibody are located on the surface of the hemichannel. As shown in FIG. 2B, an N-T-L motif from four of the six protomers of the Cx26 hemichannel play an important role in binding of the abEC1.1 antibody to the Cx26 hemichannel. As shown in FIGS. 2C-2D, the amino acids involved of the Cx26 hemichannel involved in the interaction with the abEC1.1 antibody are located on the EC1 and EC2 loops of Cx26 hemichannel. Molecular dynamics simulation was performed to further understand the interaction of the abEC1.1 antibody with the Cx26 hemichannel. As shown in FIGS. 3A-3D, both light chain and heavy chain interact with Cx26 hemichannel, and the abEC1.1 antibody interacts with different protomers of a Cx26 hemichannel.

Example 7: AbEC1.1 Antibody Inhibits Cx30A88V Homomeric Mutant Hemichannels

Figure 4:
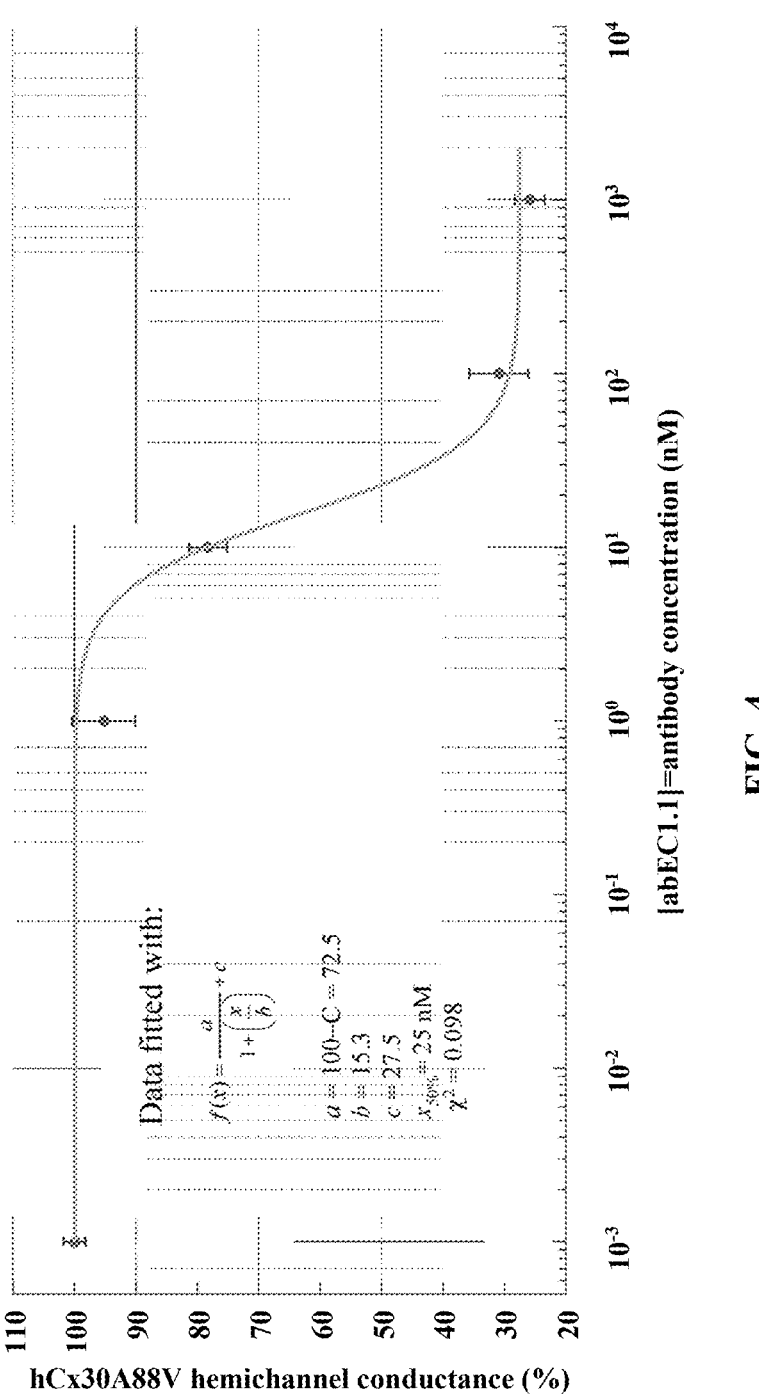
FIG. 4 shows that abEC1.1 inhibits Cx30A88V homomeric mutant hemichannels in HeLa DH transfectants. The ordinate denotes the membrane conductance, as measured with a step protocol (see FIGS. 5A-5B) and normalized to pre-antibody application levels. The abscissa represents abEC1.1 concentration (nM). Antibody was applied for 15 min from a glass micro-capillary positioned near the target cell. To facilitate fluid expulsion from the glass microcapillary, pressure was applied at its back using a pneumatic picopump (Cat. No. SYS-PV820, World Precision Instruments). Each data point is the mean±s.e.m. for n=5 cells. The solid line is the least-square fit to a modified Hill equation (shown), which yields an $IC_{50}$ of 25 nM.

To understand whether abEC1.1 antibody can inhibit mutant hemichannels, such as those found in type X Charcot-Marie-Tooth neuropathy (CMTX1; OMIM No. 302800), ectodermal dysplasia 2, Clouston type (OMIM No. 129500), or Keratitis-ichthyosis-deafness syndrome (KIDS; OMIM No. 148210), HeLa DH cells expressing Cx30-A88V homomeric hemichannel were treated with increasing doses of the abEC1.1 antibody. Membrane conductance was measured using patch clamp with a step protocol and normalized to pre-antibody application levels. As shown in FIG. 4, the abEC1.1 antibody inhibited the Cx30-A88V homomeric hemichannels with an IC$_{50}$ of 25 nM.

Figure 5A:
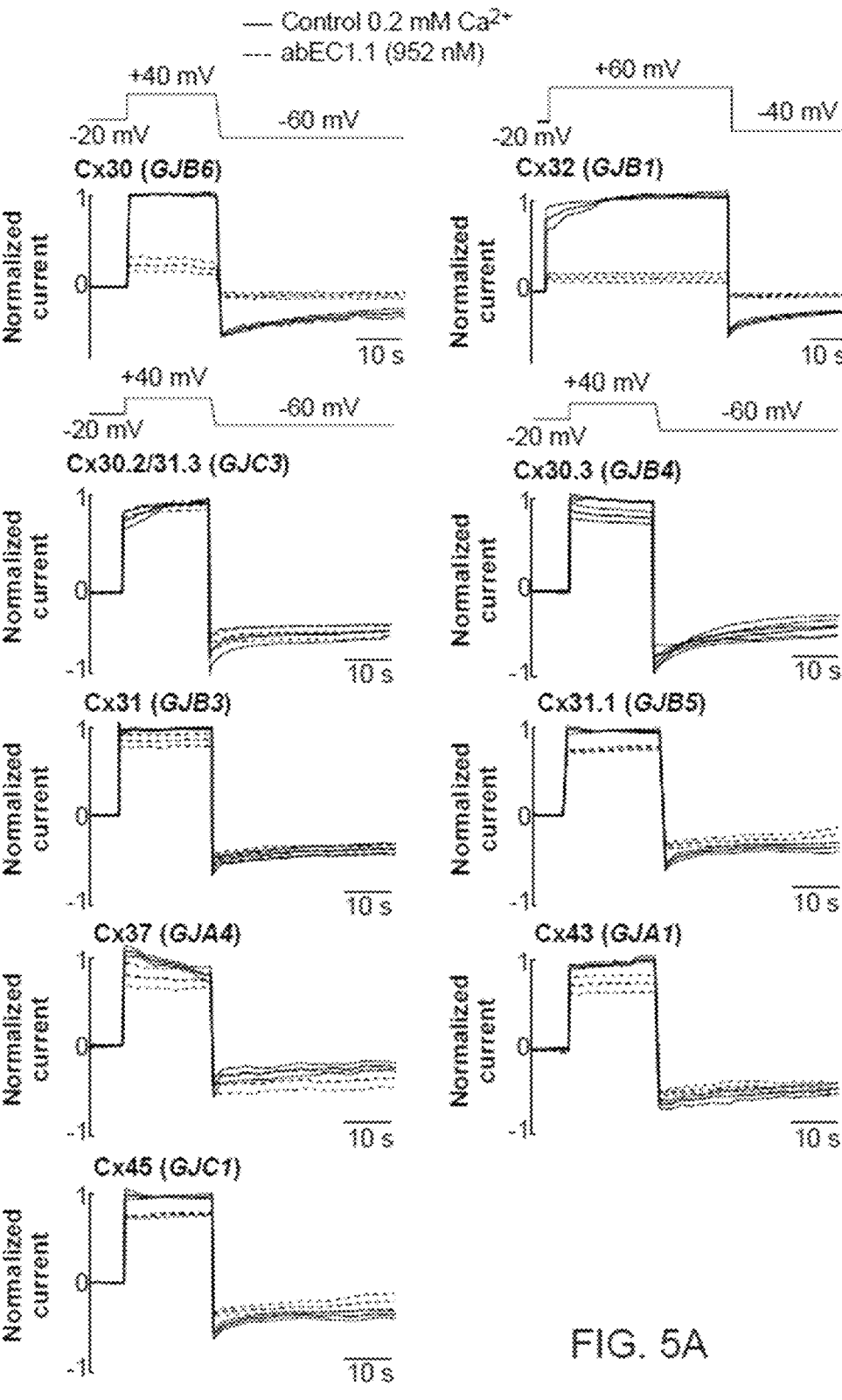
FIG. 5A shows the effects of abEC1.1 on whole patch clamp cell currents elicited by voltage commands (black traces) recorded from HeLa DH cells transiently transfected with plasmids expressing the indicated connexin. The cells were perfused with an extracellular solution containing 0.2 mM $Ca^{2+}$ concentration. Shown are mean values (thick traces)±s.e.m. (thin traces) for at least n=3 cells in each data set. Total hemichannel currents were measured before (blue traces, control) and after (green traces) pressure application for 15 minutes of abEC1.1 from a glass micro-capillary loaded with antibody at 952 nM, positioned near the target cell and driven by the pneumatic pico pump as explained herein. Currents were normalized to the mean value of the control response evoked by the application of the depolarization (positive voltage) step.
Figure 5B:
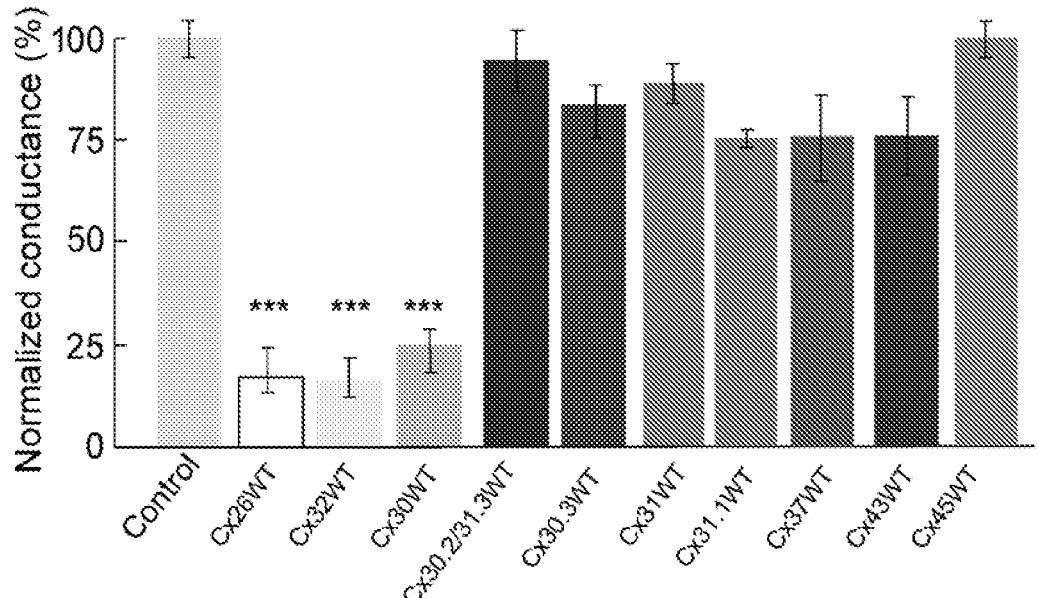
FIG. 5B shows pooled patch clamp results in a histogram form for the membrane conductance (mean±s.e.m.) as measured after 15 min of the application of abEC1.1 (952 nM), normalized to corresponding values measured before antibody application (Control) in HeLa DH cells transiently transfected with plasmids expressing the shown connexin; asterisks indicate significant difference (***, P<0.001, paired/test). Experiments were performed as in FIG. 5A.

To understand the effect of the antibody on other hemichannels, additional patch clamp experiments were performed in HeLa DH cells that expressed the following connexins: Cx30, Cx32, Cx31.3, Cx30.3, Cx31, Cx31.1, Cx37, Cx43, and Cx45. In each case, total hemichannel currents were measured before and after the application of abEC1.1. The currents measured obtained before the application of abEC1.1 served as internal negative controls for the absence of the antibody. As shown in FIG. 5A, abEC1.1 inhibited for Cx26, Cx30 and Cx32. Patch clamp results were pooled, normalized to corresponding values measured before antibody application, and compared between different connexins. As shown in FIG. 5B, the inhibition efficiency of abEC1.1 was comparable for Cx26, Cx30 and Cx32 hemichannels (additional data not shown). The Table below provides the differences from EC1 or EC2 sequences of Cx26 are shown in boldface font. Comparison of the data shown in FIG. 5B, and sequences of the EC1 and EC2 loops revealed the following. Firstly, Cx26, Cx30 and Cx32 not only have identical sequences of the EC1 and EC2 loops, but also that the EC1 and EC2 loops of the Cx26, Cx30 and Cx32 can adapt comparable 3-D configuration which allows the binding of the abEC1.1 antibody. A single amino acid difference in the EC1 and EC2 loops correlated with reduced the inhibitory effects of the antibody (compare the sequences in the Table below and patch clamp results in FIG. 5A-5B for Cx30.2/31.3, Cx30.3, Cx31, Cx31.1, Cx37, Cx43 and Cx45 hemichannels). This difference could also be attributed to the differences in 3-D configurations of the hemichannels comprising Cx30.2/31.3, Cx30.3, Cx31, Cx31.1, Cx37, Cx43 and Cx45. Plasma membrane channels composed of pannexin 1 were not affected by abEC1.1 (data not shown).

| Connexin protein | Gene name | Blosum score | Epitope | |
|---|---|---|---|---|
| | | | EC1 binding residues | EC2 binding residues |
| Cx26 | GJB2 | 0 | NTLQP (SEQ ID NO: 15) | PN (SEQ ID NO: 16) |
| Cx32 | GJB1 | 0 | NTLQP (SEQ ID NO: 17) | PN (SEQ ID NO: 18) |
| Cx30 | GJB6 | 0 | NTLQP (SEQ ID NO: 19) | PN (SEQ ID NO: 20) |
| Cx31 | GJB3 | -6 | NTKQP (SEQ ID NO: 21) | PN (SEQ ID NO: 22) |
| Cx31.1 | GJB5 | -6 | NTRQP (SEQ ID NO: 23) | PN (SEQ ID NO: 24) |
| Cx30.3 | GJB4 | -11 | NTKQP (SEQ ID NO: 35) | PH (SEQ ID NO: 36) |
| Cx37 | GJA4 | -13 | NTAQP (SEQ ID NO: 41) | P (SEQ ID NO: 42) |
| Cx43 | GJA1 | -17 | NTQQP (SEQ ID NO: 45) | PH (SEQ ID NO: 46) |
| Cx45 | GJC1 | -18 | NTEQP (SEQ ID NO: 47) | PH (SEQ ID NO: 48) |
| Cx30.2 | GJC3 | -27 | HTQQP (SEQ ID NO: 51) | LG (SEQ ID NO: 52) |

These results demonstrate that the abEC1.1 antibody can inhibit the mutant Cx26, Cx32, and/or Cx30 hemichannels. These results demonstrate that anti-Cx26 antibodies of the present technology are useful in methods for treating type X Charcot-Marie-Tooth neuropathy (CMTX1; OMIM No. 302800), ectodermal dysplasia 2, Clouston type (OMIM No. 129500), or Keratitis-ichthyosis-deafness syndrome (KIDS; OMIM No. 148210).

Example 8: Size Exclusion Chromatography Assays
to Study Antibody Aggregation

Test tubes containing 4.2 mg/mL of antibody per tube were incubated at 4° C., room temperature (~22° C.), 37° C. and 42° C. for 3, 5, 7 and 16 days. At each time point, 20 μL of solution were loaded into a Nanofilm SEC-250 column (Sepax Technologies, Inc., DW, USA) and processed at flow-rates of 0.5 mL/min using a 1290 Infinity II liquid chromatography system (Agilent Technologies, Santa Clara, CA, USA). Raw data generated by the instrument (optical density, OD, measured at 405 nm vs. retention time) were normalized to the peak of each chromatogram and plotted using OriginPro 2017 software (OriginLab, Northampton, MA, USA).

Figures 6A, 6B:
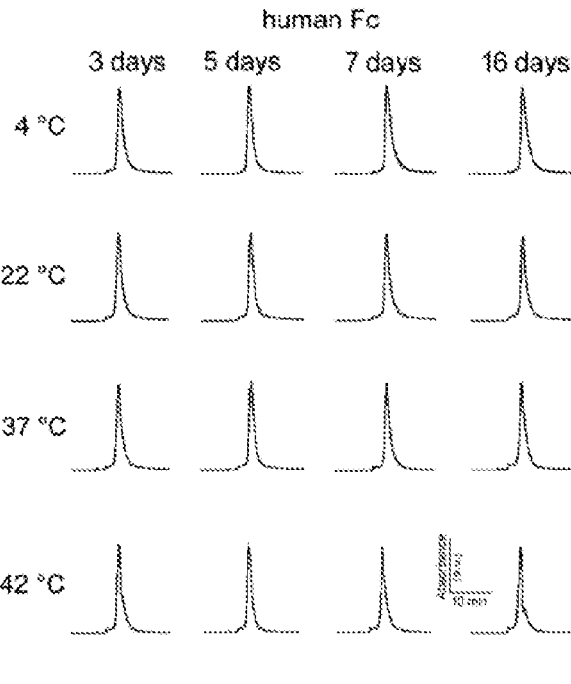
FIG. 6A shows the peak-normalized size-exclusion chromatography (SEC) profiles of the diabody having a human Fc domain (abEC1.1). The antibody was incubated under the indicated storage conditions and analyzed. Each line graph is a chromatographic profile as measured by absorbance at 405 nm and plotted as a function of retention time. These data demonstrate minimal or no aggregation for up to 16 days at temperatures between 4° C. and 37° C.
FIG. 6B shows peak-normalized size-exclusion chromatography (SEC) profiles of the murine chimeric IgG1 version of abEC1.1 (abEC1.1m). Experiments were performed as in FIG. 6A. These data demonstrate minimal or no aggregation for up to 16 days at temperatures between 4° C. and 37° C., although abEC1.1m has a higher tendency to aggregate compared to abEC1.1, as indicated by the appearance of multiple peaks for abEC1.1m held at 42° C. for 16 days.

As shown in FIG. 6A, there was minimal or no aggregation of a diabody having a human Fc domain (abEC1.1) for up to 16 days at temperatures between 4° C. and 37° C. As shown in FIG. 6B, abEC1.1m has a higher tendency to aggregate for compared to abEC1.1, as indicated by the appearance of multiple peaks for abEC1.1m held at 42° C. for 16 days. These results suggest that abEC1.1 and abEC1.1m would be stable if formulated in a pharmaceutical formulation.

Example 9: Pharmacokinetics (PK) Profile of
abEC1.1

All animal experimentation was conducted in adherence to the NIH Guide for the Care and Use of Laboratory Animals. All mice (*Mus musculus*) were bred under Specific and Opportunistic Pathogen-Free (SOPF) conditions in Shanghai Biomodel Organism Science & Technology Development Co., Ltd., Shanghai (China), shortened as ShBio, under animal production license sxck (Shanghai) 2017-010. All in vivo experiments were performed at ShBio under animal usage license: sxck (Shanghai) 2017-012. Both male and female mice, aged 6 to 8 weeks, were treated either topically or systemically (see below).

For systemic delivery, antibody was dissolved in 100 μl of sterile PBS (5 mg of antibody per kg of mouse weight) and delivered as single bolus via caudal vein injection. Antibody concentration in serum was measured by ELISA at various time points post de livery.

As shown in FIG. 7, abEC1.1m antibody, the murine chimeric IgG1 version, shows more gradual decline in mouse serum concentration, compared to abEC1.1. It is likely that Fc domains of the murine IgG1 impart greater stability to the abEC1.1m antibody in mice.

Since topical administration of the abEC1.1 antibody is envisioned, pharmacokinetics was also assessed following topical administration. For these measurements, 100 μl of 50 μg/ml antibody dispersed in cetomacrogol cream was massaged until completely absorbed in the depilated skin of the mouse back. Summarily, for topical delivery, animals were depilated on the back under gaseous anesthesia (2% Isofluorane). The administration was carried out with antibody incorporated in cetomacrogol base cream (100 μl, 50 μg of antibody per ml of cream; ingredients: Aqua, Petrolatum, Paraffinum Liquidum, Cetyl Alcohol, Stearyl Alcohol, Ceteareth-20, Sodium Benzoate, Potassium Sorbate, Benzyl Alcohol, Disodium EDTA, Citric Acid.

Administration of antibody dispersed in cream required a light massage under anesthesia (2% Isofluorane), to allow the cream to be absorbed by the skin of the animal. Antibody concentration in skin protein extract was assessed at various time points by ELISA in freshly excised skin samples harvested up to 24 hours post-delivery.

Figure 8:
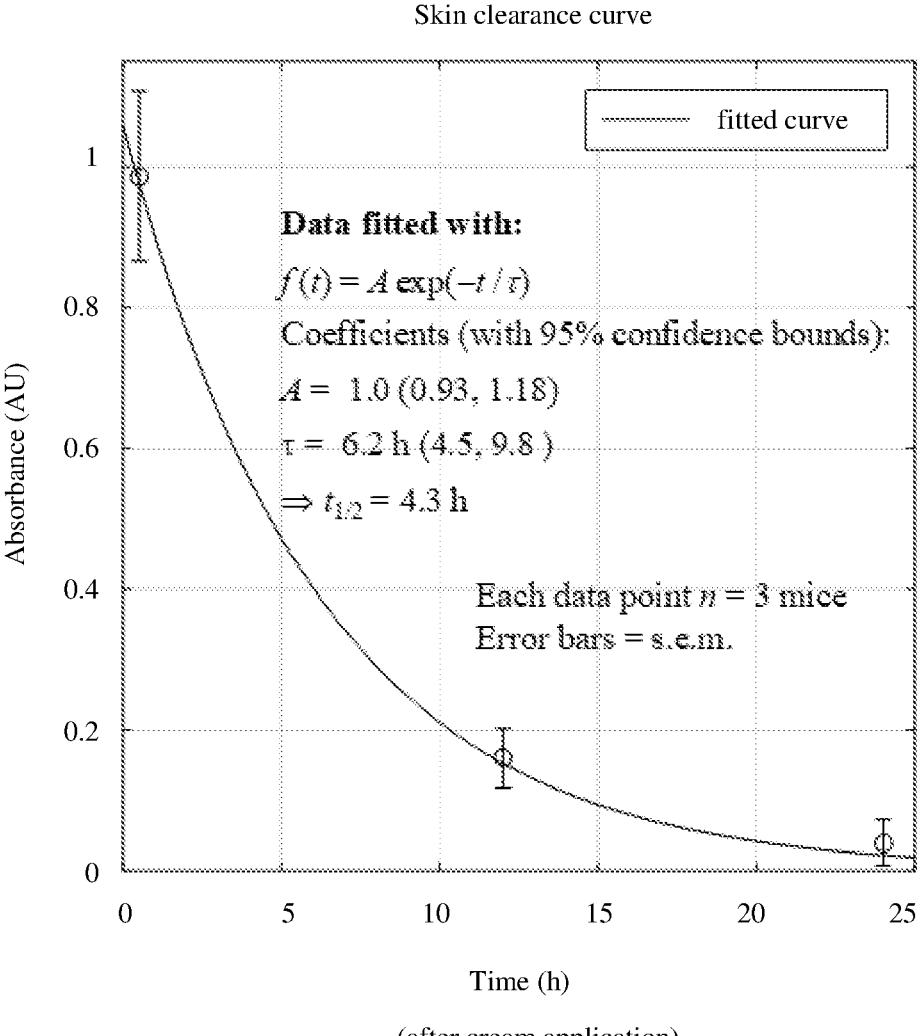
FIG. 8 shows the persistence of the abEC1.1 antibody in the epidermis of a wild type mouse strain (C57BL6/N) following topical administration at time 1=0. The ordinate plots the antibody concentrations as measured by ELISA. For these measurements, mice were humanely euthanized 30 min, 12 hours and 24 hours post treatment. Data were obtained from n=3 mice per time point; age: from 6 to 8 weeks; preparation: antibody dispersed in cetomacrogol

Antibody concentrations were measured by ELISA in skin protein extracts at 30 min, 12 hour and 24 hours post treatment. As shown in FIG. 8, the abEC1.1 antibody persisted following topical administration with a $t_{1/2}$ of 4.3 hr.

Example 10: Efficacy of the abEC1.1 Antibody in
Homozygous Cx30A88V (Cx30$^{A88V/A88V}$) Mice Mutations in the GJB6 gene, that codes for Cx30, including the A88V mutation, has been linked causally to Ectodermal dysplasia 2, also known as Clouston syndrome (OMIM No. 129500). The mice harboring the Cx30$^{A88V/A88V}$ mutation (Cx30A88V) is the only currently available mouse model of Clouston syndrome. To confirm previously reported phenotype, sebaceous glands were visualized by confocal microscopy following staining with Nile red, a marker for intracellular lipids, which detects lipid-filled sebocytes. As shown in FIG. 9, a representative sebaceous gland was hypertrophic, featuring increased sebocyte number compared to a wild type mouse (data not shown).

Modeling studies demonstrated that the abEC1.1 antibody specifically bound to the EC1 and EC2 loops of Cx30, Cx26, and Cx32, but not Cx30.2/31.3, Cx30.3, Cx31, Cx31.1, Cx37, Cx43 and Cx45 (See Examples 1~4 supra). Specific binding is necessary but not sufficient for a specific pharmacological effect. To understand whether the specific binding translates to a pharmacological effect, Cx30$^{+/+}$ (wild type) and homozygous Cx30$^{A88V/A88V}$ mutant mice were treated with vehicle only, the abEC1.1 antibody, or W104S mutant of the abEC1.1 antibody. Cx30$^{+/+}$ (wild type) mice served as a negative control for lack of Clouston Syndrome. The W104S mutant of the abEC1.1 antibody, having mutation of the W104 residue of CDR3, served as a negative control.

All animal experimentation was conducted in adherence to the NIH Guide for the Care and Use of Laboratory Animals. All mice (*Mus musculus*) were bred under Specific and Opportunistic Pathogen-Free (SOPF) conditions in Shanghai Biomodel Organism Science & Technology Development Co., Ltd., Shanghai (China), shortened as ShBio, under animal production license sxck (Shanghai) 2017-010. All in vivo experiments were performed at ShBio under animal usage license: sxck(Shanghai)2017-012.

Mice were allocated to the different treatment groups by weight, gender, and littermate randomization. Animal caretakers and investigators conducting the preclinical efficacy studies and investigators conducting the assessment of outcomes were blinded to the treatment allocation.

For topical treatment, animals were depilated on the back under gaseous anesthesia (2% Isofluorane) at the beginning of treatment. The administration was carried daily out with antibody incorporated in cetomacrogol base cream (100 μl, 50 μg of antibody per ml of cream; ingredients: as above) by light massage under anesthesia (2% Isofluorane), to allow the cream to be absorbed by the skin of the animal.

For systemic treatment, antibody was dissolved in 100 μl of sterile PBS (10 mg of antibody per kg of mouse weight) and delivered via IP injection at intervals of 3 days.

Both topical and systemic treatment lasted two weeks, thereafter mice were humanely euthanized and processed for histology or other ex vivo measurement procedures aimed at assessing the efficacy of treatment.

As shown in FIG. 10 (left panel), Cx30$^{A88V/A88V}$ mice had significantly more sebocytes per sebaceous gland compared to the wild type mice. As shown in FIG. 10 (middle panel), topical administration of the abEC1.1 antibody resulted in a significant decrease in sebocytes per sebaceous gland compared to both untreated or W104S mutant-treated Cx30$^{488V/488V}$ mutant mice. Both the abEC1.1 antibody and the W104S mutant had no effect on the number of sebocytes per sebaceous gland in wild type mice. As shown in FIG. 10 (right panel), systemic administration of the abEC1.1m antibody also resulted in a significant decrease in sebocytes per sebaceous gland compared to untreated Cx30$^{488V/488V}$ mutant mice.

To further understand the basis for the observed significant decrease in sebocytes per sebaceous gland compared to untreated Cx30$^{488V/488V}$ mutant mice following administration of the abEC1.1 or abEC1.1m antibodies, transversal sections of mouse dorsal skin were stained with an antibody that binds Ki-67. As shown in FIG. 11A, the Cx30$^{488V/488V}$ mice treated with abEC1.1 cream showed reduced expression of the Ki-67 proliferation marker in the skin of for two weeks, compared to the Cx30$^{488V/488V}$ mice treated with the W104S mutant of the abEC1.1 antibody. The Ki-67 fluorescence was quantitated and normalized. As shown in FIG. 11B, Cx30$^{488V/488V}$ sebaceous glands exhibited significantly ($p<0.001$) increased Ki-67 staining compared to the Cx30$^{+/+}$ mice. Further, as shown in FIG. 11B, the abEC1.1 antibody significantly reduced the Ki-67 fluorescence compared to both untreated or W104S mutant-treated Cx30$^{488V/488V}$ mutant mice. These data suggested that the abEC1.1 antibody decreased cell proliferation in sebaceous glands of Cx30$^{488V/488V}$ Clouston Syndrome mice.

Additional data show that the abEC1.1 antibody is effective in cells expressing KIDS mutant Cx26G45E and Cx26D50N (data not shown).

Further, computer simulations suggest abEC1.1 of is effective in mouse models of CMTX1 (data not shown).

These results demonstrate that the abEC1.1 antibody can inhibit the mutant Cx26, Cx32, and/or Cx30 hemichannels. These results demonstrate that anti-Cx26 antibodies of the present technology are useful in methods for treating type X Charcot-Marie-Tooth neuropathy (CMTX1; OMIM No. 302800), ectodermal dysplasia 2, Clouston type (OMIM No. 129500), or Keratitis-ichthyosis-deafness syndrome (KIDS; OMIM No. 148210).

Example 11: Statistics

For normally distributed data, statistical comparisons of means data were made by Student's two-tailed t-test using a worksheet (Microsoft Office Excel 2017, Version 1.30), whereas ANOVA and post-hoc comparison by Tuckey's test were used to analyze the differences among group means using Statistica (version 6.0, Statsoft Inc.). The same software was also used to perform the Mann-Whitney U-test on data that did not require the assumption of normal distribution. Mean values are quoted±standard error of the mean (s.e.m.) where p-values <0.05 indicate statistical significance.

EQUIVALENTS

The present technology is not to be limited in terms of the particular embodiments described in this application, which are intended as single illustrations of individual aspects of the present technology. Many modifications and variations of this present technology can be made without departing from its spirit and scope, as were apparent to those skilled in the art. Functionally equivalent methods and apparatuses within the scope of the present technology, in addition to those enumerated herein, were apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As were understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as were understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

---

The invention claimed is:

1. A method for treating ectodermal dysplasia 2, Clouston type (OMIM No. 129500) in a subject in need thereof, comprising administering to the subject an effective amount of an antibody or antigen binding fragment thereof comprising a heavy chain immunoglobulin variable domain $(V_H)$ and a light chain immunoglobulin variable domain $(V_L)$, wherein the $V_H$ comprises complementarity determining regions $V_H$ CDR1, $V_H$ CDR2 and $V_H$ CDR3, wherein the $V_H$ CDR1 comprises an amino acid sequence set forth in SEQ ID NO: 3, $V_H$ CDR2 comprises an amino acid sequence set forth in SEQ ID NO: 4, and $V_H$ CDR3 comprises an amino acid sequence set forth in SEQ ID NO: 5; and wherein the VL comprises complementarity determining regions $V_L$ CDR1, $V_L$ CDR2 and $V_L$ CDR3, wherein the $V_L$ CDR1 comprises an amino acid sequence set forth in SEQ ID NO: 6, $V_L$ CDR2 comprises an amino acid sequence set forth in SEQ ID NO: 7, and $V_L$ CDR3 comprises an amino acid sequence set forth in SEQ ID NO: 8.

2. The method of claim 1, wherein the method alleviates one or more symptoms of ectodermal dysplasia 2, Clouston type (OMIM No. 129500) selected from the group consisting of dystrophy of the nails, hypoplasticity and deformation of nails, and increased susceptibility to paronychial infections.

3. The method of claim 1, wherein the $V_H$ comprises an amino acid sequence set forth in SEQ ID NO: 11.

4. The method of claim 1, wherein the $V_L$ comprises an amino acid sequence set forth in SEQ ID NO: 12.

5. The method of claim 1, wherein the antibody or antigen binding fragment thereof is administered by a route selected from the group consisting of parenteral, oral, inhalation, topical, intraocular, iontophoretic, and transmucosal administration.

6. The method of claim 1, wherein the antibody or antigen binding fragment thereof is administered by a parenteral route.

7. The method of claim 1, wherein the antibody or antigen binding fragment thereof is administered by a topical route.

8. The method of claim 1, wherein the antibody or antigen binding fragment thereof is an antibody, scFv, (scFv)$_2$, scFv-Fc, Fab, Fab', F(ab')$_2$ or an scFv-Fc antibody.

9. The method of claim 1, wherein the antibody or antigen binding fragment thereof is an scFv-Fc antibody.

10. The method of claim 1, wherein the antibody or antigen binding fragment thereof is formulated as an ointment, salve, gel, or cream.

11. The method of claim 1, wherein the antibody or antigen binding fragment thereof is formulated as an injectable.

\* \* \* \* \*

SEQUENCE LISTING

```
<160> NUMBER OF SEQ ID NOS: 53

<210> SEQ ID NO 1
<211> LENGTH: 5
<212> TYPE: PRT
<213> ORGANISM: Homo sapiens

<400> SEQUENCE: 1
```

-continued

```
Asn Thr Leu Gln Pro
1               5

<210> SEQ ID NO 2
<211> LENGTH: 2
<212> TYPE: PRT
<213> ORGANISM: Homo sapiens

<400> SEQUENCE: 2

Pro Asn
1

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Phe Thr Phe Ser Ser Tyr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Ser His Gly Gly Ser Asn Lys
1               5

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Arg Asp Phe Ser Trp Arg Gly Tyr Tyr Met Asp Val
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Ser Ile Ser Ser Tyr
1               5

<210> SEQ ID NO 7
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 7

Gly Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Tyr Gly Ser Ser Pro Arg Thr
1               5

<210> SEQ ID NO 9
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
caggtacagc tgcagcagtc aggggggggc gtggtccagc ctgggaggtc cctgagactc      60
tcctgtgcag cctctggatt caccttcagt agctatgcta tgcactgggt ccgccaggct     120
ccaggcaagg ggctggagtg ggtggcagtt atatcacatg gtggaagtaa taaatactac     180
gcagactccg tgaagggccg attcaccatc tccagagaca attccaagaa cacgctgtat     240
ctgcaaatga acagcctgag agctgaggac acggctgtgt attactgtgc gagagatttt     300
agttggagag ggtactacat ggacgtctgg ggcaaaggca ccctggtcac cgtctcctca     360

<210> SEQ ID NO 10
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gaaacgacac tcacgcagtc tccagccacc ctgtctttgt ctccagggga aagagccacc      60
ctctcctgca gggccagtca gagtattagc agctacttag cctggtacca gcagaaacct     120
ggccaggctc ccaggctcct catctatggt gcatccacca gggccactgg catcccagac     180
aggttcagtg gcagtgggtc tgggacagac ttcactctca ccatcagcag actggagcct     240
gaagattttg cagtgtatta ctgtcagcag tatggtagct cacctcgaac tttcggcgga     300
gggaccaagg tggaaatcaa acgt                                            324

<210> SEQ ID NO 11
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Gln Ser Gly Gly Gly Val Val Gln Pro Gly Arg
1               5                   10                  15

-continued

```
Ser Leu Arg Leu Ser Cys Ala Ala Ser Gly Phe Thr Phe Ser Ser Tyr
          20                  25                  30

Ala Met His Trp Val Arg Gln Ala Pro Gly Lys Gly Leu Glu Trp Val
          35                  40                  45

Ala Val Ile Ser His Gly Gly Ser Asn Lys Tyr Tyr Ala Asp Ser Val
      50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
              85                  90                  95

Ala Arg Asp Phe Ser Trp Arg Gly Tyr Tyr Met Asp Val Trp Gly Lys
              100                 105                 110

Gly Thr Leu Val Thr Val Ser Ser
          115                 120
```

```
<210> SEQ ID NO 12
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12
```

```
Glu Thr Thr Leu Thr Gln Ser Pro Ala Thr Leu Ser Leu Ser Pro Gly
1                  5                   10                  15

Glu Arg Ala Thr Leu Ser Cys Arg Ala Ser Gln Ser Ile Ser Ser Tyr
              20                  25                  30

Leu Ala Trp Tyr Gln Gln Lys Pro Gly Gln Ala Pro Arg Leu Leu Ile
          35                  40                  45

Tyr Gly Ala Ser Thr Arg Ala Thr Gly Ile Pro Asp Arg Phe Ser Gly
      50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Arg
              85                  90                  95

Thr Phe Gly Gly Gly Thr Lys Val Glu Ile Lys Arg
              100                 105
```

```
<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
```

```
ggtcgaagga acctttcaca gg                                            22
```

```
<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
```

```
gctaccatca cgtgctcttt gg                                            22
```

```
<210> SEQ ID NO 15
<211> LENGTH: 5
<212> TYPE: PRT
<213> ORGANISM: Homo sapiens

<400> SEQUENCE: 15

Asn Thr Leu Gln Pro
1               5

<210> SEQ ID NO 16
<211> LENGTH: 2
<212> TYPE: PRT
<213> ORGANISM: Homo sapiens

<400> SEQUENCE: 16

Pro Asn
1

<210> SEQ ID NO 17
<211> LENGTH: 5
<212> TYPE: PRT
<213> ORGANISM: Homo sapiens

<400> SEQUENCE: 17

Asn Thr Leu Gln Pro
1               5

<210> SEQ ID NO 18
<211> LENGTH: 2
<212> TYPE: PRT
<213> ORGANISM: Homo sapiens

<400> SEQUENCE: 18

Pro Asn
1

<210> SEQ ID NO 19
<211> LENGTH: 5
<212> TYPE: PRT
<213> ORGANISM: Homo sapiens

<400> SEQUENCE: 19

Asn Thr Leu Gln Pro
1               5

<210> SEQ ID NO 20
<211> LENGTH: 2
<212> TYPE: PRT
<213> ORGANISM: Homo sapiens

<400> SEQUENCE: 20

Pro Asn
1

<210> SEQ ID NO 21
<211> LENGTH: 5
<212> TYPE: PRT
<213> ORGANISM: Homo sapiens

<400> SEQUENCE: 21

Asn Thr Lys Gln Pro
1               5
```

```
<210> SEQ ID NO 22
<211> LENGTH: 2
<212> TYPE: PRT
<213> ORGANISM: Homo sapiens

<400> SEQUENCE: 22

Pro Asn
1

<210> SEQ ID NO 23
<211> LENGTH: 5
<212> TYPE: PRT
<213> ORGANISM: Homo sapiens

<400> SEQUENCE: 23

Asn Thr Arg Gln Pro
1               5

<210> SEQ ID NO 24
<211> LENGTH: 2
<212> TYPE: PRT
<213> ORGANISM: Homo sapiens

<400> SEQUENCE: 24

Pro Asn
1

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31
```

```
000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35
<211> LENGTH: 5
<212> TYPE: PRT
<213> ORGANISM: Homo sapiens

<400> SEQUENCE: 35

Asn Thr Lys Gln Pro
1               5

<210> SEQ ID NO 36
<211> LENGTH: 2
<212> TYPE: PRT
<213> ORGANISM: Homo sapiens

<400> SEQUENCE: 36

Pro His
1

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41
<211> LENGTH: 5
<212> TYPE: PRT
<213> ORGANISM: Homo sapiens
```

```
<400> SEQUENCE: 41

Asn Thr Ala Gln Pro
1               5

<210> SEQ ID NO 42
<211> LENGTH: 1
<212> TYPE: PRT
<213> ORGANISM: Homo sapiens

<400> SEQUENCE: 42

Pro
1

<210> SEQ ID NO 43

<400> SEQUENCE: 43

000

<210> SEQ ID NO 44

<400> SEQUENCE: 44

000

<210> SEQ ID NO 45
<211> LENGTH: 5
<212> TYPE: PRT
<213> ORGANISM: Homo sapiens

<400> SEQUENCE: 45

Asn Thr Gln Gln Pro
1               5

<210> SEQ ID NO 46
<211> LENGTH: 2
<212> TYPE: PRT
<213> ORGANISM: Homo sapiens

<400> SEQUENCE: 46

Pro His
1

<210> SEQ ID NO 47
<211> LENGTH: 5
<212> TYPE: PRT
<213> ORGANISM: Homo sapiens

<400> SEQUENCE: 47

Asn Thr Glu Gln Pro
1               5

<210> SEQ ID NO 48
<211> LENGTH: 2
<212> TYPE: PRT
<213> ORGANISM: Homo sapiens

<400> SEQUENCE: 48

Pro His
1

<210> SEQ ID NO 49

<400> SEQUENCE: 49
```

-continued

```
000

<210> SEQ ID NO 50

<400> SEQUENCE: 50

000

<210> SEQ ID NO 51
<211> LENGTH: 5
<212> TYPE: PRT
<213> ORGANISM: Homo sapiens

<400> SEQUENCE: 51

His Thr Gln Gln Pro
1               5

<210> SEQ ID NO 52
<211> LENGTH: 2
<212> TYPE: PRT
<213> ORGANISM: Homo sapiens

<400> SEQUENCE: 52

Leu Gly
1

<210> SEQ ID NO 53
<211> LENGTH: 16
<212> TYPE: PRT
<213> ORGANISM: Homo sapiens

<400> SEQUENCE: 53

Lys Glu Val Trp Gly Asp Glu Gln Ala Asp Phe Val Cys Asn Thr Leu
1               5                   10                  15
```